(12) United States Patent
Wang et al.

(10) Patent No.: US 9,885,038 B2
(45) Date of Patent: Feb. 6, 2018

(54) GENE SILENCING METHODS

(71) Applicant: Commonwealth Scientific and Industrial Research Organisation, Acton (AU)

(72) Inventors: Ming-Bo Wang, Canberra (AU); Peter Waterhouse, Paddington (AU)

(73) Assignee: Commonwealth Scientific & Industrial Research Organisation, Acton (AU)

(*) Notice: Subject to any disclaimer, the term of this patent is extended or adjusted under 35 U.S.C. 154(b) by 77 days.

(21) Appl. No.: 14/659,932

(22) Filed: Mar. 17, 2015

(65) Prior Publication Data

US 2015/0259682 A1 Sep. 17, 2015

Related U.S. Application Data

(63) Continuation of application No. 12/673,428, filed as application No. PCT/AU2008/001180 on Aug. 14, 2008, now abandoned.

(60) Provisional application No. 61/013,604, filed on Dec. 13, 2007.

(30) Foreign Application Priority Data

Aug. 14, 2007 (EP) .................................... 07015956

(51) Int. Cl.
| | |
|---|---|
| *C12N 15/82* | (2006.01) |
| *A01H 5/00* | (2006.01) |
| *C12N 15/113* | (2010.01) |
| *C12N 15/11* | (2006.01) |
| *C12N 15/63* | (2006.01) |
| *A61K 31/713* | (2006.01) |

(52) U.S. Cl.
CPC .......... *C12N 15/113* (2013.01); *A61K 31/713* (2013.01); *C12N 15/111* (2013.01); *C12N 15/63* (2013.01); *C12N 2310/14* (2013.01); *C12N 2320/50* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 6,423,885 B1 | 7/2002 | Waterhouse et al. | |
| 2004/0029275 A1 | 2/2004 | Brown et al. | |
| 2005/0155102 A1 | 7/2005 | Gruis et al. | |
| 2007/0111227 A1 | 5/2007 | Green et al. | |
| 2010/0192237 A1 | 7/2010 | Sue et al. | |

FOREIGN PATENT DOCUMENTS

| | | |
|---|---|---|
| WO | WO 89/03887 A1 | 5/1989 |
| WO | WO 89/10396 A1 | 11/1989 |
| WO | WO 92/13956 A1 | 8/1992 |
| WO | WO 96/06932 A1 | 3/1996 |
| WO | WO 97/13865 A1 | 4/1997 |
| WO | WO 98/53083 A1 | 11/1998 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 00/01846 A1 | 1/2000 |
| WO | WO 00/44914 A1 | 8/2000 |
| WO | WO 00/49035 A1 | 8/2000 |
| WO | WO 01/12824 A1 | 2/2001 |
| WO | WO 03/076619 A1 | 9/2003 |
| WO | WO 2004/073390 A1 | 9/2004 |
| WO | WO 2005/026356 A1 | 3/2005 |
| WO | WO 2006/042112 A2 | 4/2006 |
| WO | WO 2007/033436 A1 | 3/2007 |
| WO | WO 2007/048629 A2 | 5/2007 |
| WO | WO 2007/128052 A1 | 11/2007 |

OTHER PUBLICATIONS

Nagano et al, 2013, Nucleic Acids Research, 42:1845-1856.*
Grimm et al, 2006, Nature, 441:537-541.*
Notification Concerning Transmittal of International Preliminary Report on Patentability dated Feb. 25, 2010, and International Preliminary Report on Patentability dated Feb. 16, 2010, issued by the International Bureau of WIPO in corresponding International Patent Application No. PCT/AU2008/001180.
Written Opinion of the International Searching Authority dated Oct. 10, 2008, issued by the Australian Patent Office in corresponding International Patent Application No. PCT/AU2008/001180.
An et al., *Conserved Expression of the Arabidopsis ACT1 and ACT3 Actin Subclass in Organ Primordia and Mature Pollen*, 8 The Plant Cell 15-30 (Jan. 1996).
Colman, *Production of therapeutic proteins in the milk of transgenic livestock*, 63 Biochemical Society Symposia 141-147 (1998).
Dalrymple et al., *Genetically Modified Livestock for the Production of Human Proteins in Milk*, 15 Biotechnology and Genetic Engineering Reviews 33-49 (Apr. 1998).
Dunoyer et al., *Dicer-Like 4 is required for RNA interference and produces the 21-nucleotide small interfering RNA component of the plant cell-to-cell silencing signal*, 37(12) Nature Genetics 1356-1360 (Dec. 2005).

(Continued)

*Primary Examiner* — Jason Deveau Rosen
(74) *Attorney, Agent, or Firm* — Buchanan Ingersoll & Rooney PC

(57) ABSTRACT

Provided are methods and means to obtain improved gene silencing of target nucleic acids whereby at least two inhibitory RNA molecules are provided which are targeted to the same nucleic acid, but which are processed into short interfering RNA molecules through different processing pathways. Also provided are methods and means to obtain improved gene silencing of target nucleic acids whereby at least two inhibitory RNA molecules are provided which are targeted to different nucleic acids, but which are processed into short interfering RNA molecules through different processing pathways.

23 Claims, 4 Drawing Sheets

(56) References Cited

OTHER PUBLICATIONS

Dunoyer et al., *Intra- and intercellular RNA interference in Arabidopsis thaliana requires components of the microRNA and heterochromatic silencing pathways*, 39(7) Nature Genetics 848-856 (Jul. 2007).
Fire et al., *Potent and specific genetic interference by double-stranded RNA in Caenorhabditis elegans*, 391 Nature 806-811 (Feb. 19, 1998).
Gasciolli et al., *Partially Redundant Functions of Arabidopsis Dicer-like Enzymes and a Role for DCL4 in Producing trans-Acting siRNAs*, 15 Current Biology 1494-1500 (Aug. 23, 2005).
Hamilton et al., *A transgene with repeated DNA causes high frequency, post-transcriptional suppression of ACC-oxidase gene expression in tomato*, 15(6) The Plant Journal 737-746 (1998).
Han et al., *Molecular Basis for the Recognition of Primary microRNAs by the Drosha-DGCR8 Complex*, 125 Cell 887-901 (Jun. 2, 2006).
Harpster et al., *Relative strengths of the 35S califlower mosaic virus, 1', 2', and nopaline synthase promoters in transformed tobacco sugarbeet and oilseed rape callus tissue*, 212 Molecular and General Genetics 182-190 (1988).
Hudspeth et al., *Structure and expression of the maize gene encoding the phosphoenolpyruvate carboxylase isozyme involved in $C_4$ photosynthesis*, 12 Plant Molecular Biology 579-589 (1989).
Kameda et al., *A hypothermic-temperature-sensitive gene silencing by the mammalian RNAi*, 315 Biochemical and Biophysical Research Communications 599-602 (2004).
Keil et al., *Both wound-inducible and tuber-specific expression are mediated by the promoter of a single member of the potato proteinase inhibitor II gene family*, 8(5) 1323-1330 (1989).
Keller et al., *Glycine-rich cell wall proteins in bean: gene structure and association of the protein with the vascular system*, 7(12) The EMBO Journal 3625-3633 (1988).
Keller et al., *Specific expression of a novel cell wall hydroxyproline-rich glycorprotein gene in lateral root initiation*, 3 Genes and Development 1639-1646 (1989).
Kurihara et al., *Arabidopsis mirco-RNA biogenesis through Dicer-like 1 protein functions*, 101(34) Proceedings of the National Academy of Sciences 12753-12758 (Aug. 24, 2004).
Lamontagne et al., *The N-Terminal Domain That Distinguishes Yeast from Bacterial RNase III Contains a Dimerization Signal Required for Efficient Double-Stranded RNA Cleavage*, 20(4) Molecular and Cellular Biology 1104-1115 (Feb. 2000).
Lee et al. *The C. elegans Heterochronic Gene lin-4 Encodes Small RNAs with Antisense Complementarity to lin-14*, 75 Cell 843-854 (Dec. 3, 1993).
Niu et al., *Expression of artificial microRNAs in transgenic Arabidopsis thaliana confers virus resistance*, 24 Nature Biotechnology 1-9 (Oct. 22, 2006).
Peleman et al., *Structure and expression analyses of the S-adenosylmethionine synthetase gene family in Arabidopsis thaliana*, 84 Gene 359-369 (1989).
Perry et al., *Transgenesis in chickens*, 2 Transgenic Research 125-133 (1993).
Pham et al., *A Dicer-2-Dependent 80S Complex Cleaves Targeted mRNAs during RNAi in Drosophila*, 117 Cell 83-94 (Apr. 2, 2004).
Qi et al., *Biochemical Specialization within Arabidopsis RNA Silencing Pathways*, 19 Molecular Cell 421-428 (Aug. 5, 2005).
Rudolph, *Biopharmaceutical production in transgenic livestock*, 17 Tibtech 367-374 (Sep. 1999).
Schwab et al., *Highly Specific Gene Silencing by Artificial MicroRNAs in Arabidopsis*, 18 The Plant Cell 1121-1133 (May 2006).
Smith et al., *Total silencing by intron-spliced hairpin RNAs*, 407 Nature 319-320 (Sep. 21, 2000).
Szittya et al., *Low temperature inhibits RNA silencing-mediated defence by the control of siRNA generation*, 22(3) The EMBO Journal 633-640 (2003).
Waterhouse et al., *Virus resistance and gene silencing in plants can be induced by simultaneous expression of sense and antisense RNA*, 95 Proceeding of the National Academy of Sciences 13959-13964 (1998).
Wilmut et al., *Embryonic and somatic cell cloning*, 10 Reproduction, Fertility, and Development 639-643 (1998).
Wilmut et al., *Viable offspring derived from fetal and adult mammalian cells*, 385 Nature 810-813 (Feb. 1997).
Xie et al., *Dicer-Like 4 functions in trans-acting small interfering RNA biogenesis and vegetative phase change in Arabidopsis thaliana*, 102(36) Proceedings of the National Academy of Sciences 12984-12989 (Sep. 6, 2005).
Xie et al., *Genetic and Functional Diversification of Small RNA Pathways in Plants*, 2(5) PLoS Biology 0642-0652 (May 2004).
Yoshikawa et al., *A pathway for the biogenesis of trans-acting siRNAs in Arabidopsis*, 19 Genes and Development 2164-2175 (2005).
Zuker, *Mfold web server for nucleic acid folding and hybridization prediction*, 31(13) Nucleic Acids Research 3406-3415 (2003).
Genbank Accession # AAZ80387, http://www.ncbi.nlm.nih.gov/protein/AAZ80387, (Sep. 7, 2005).
Genbank Accession # AJ290403, http://www.ncbi.nlm.nih.gov/nuccore/ AJ290403 (Nov. 15, 2007).
Genbank Accession # AJ236703, http://www.ncbi.nlm.nih.gov/nuccore/ AJ236703 (Mar. 3, 2003).
Genbank Accession # AJ236704, http://www.ncbi.nlm.nih.gov/nuccore/ AJ236704 (Jan. 28, 2000).
Genbank Accession # AJ236705, http://www.ncbi.nlm.nih.gov/entrez/viewer.fcgi?db=nucleotide&val=4691275 (Jan. 28, 2000).
Genbank Accession # AJ236706, http://www.ncbi.nlm.nih.gov/entrez/viewer.fcgi?db=nucleotide&val=4691276 (Jan. 28, 2000).
Genbank Accession # AT4G14210, http://www.arabidopsis.org/servlets/TairObject?type=locus&name=AT4G14210 (May 2, 2003).
Genbank Accession # EF193580, http://www.ncbi.nlm.nih.gov/nuccore/EF193580 (Jul. 3, 2007).
Genbank Accession # NP_001078101, http://www.ncbi.nlm.nih.gov/protein/NP_001078101 (Aug. 21, 2009).
Genbank Accession # P84634, http://www.ncbi.nlm.nih.gov/protein/P84634 (Apr. 5, 2011).
Genbank Accession # Q9SP32, http://www.ncbi.nlm.nih.gov/protein/Q9SP32 (Apr. 5, 2011).
Genbank Accession # S83742, http://www.ncbi.nlm.nih.gov/nuccore/S83742 (May 7, 1993).
Genbank Accession # X04788, http://www.ncbi.nlm.nih.gov/nuccore/X04788 (Nov. 15, 2007).
Genbank Accession # X14411, http://www.ncbi.nlm.nih.gov/nuccore/X14411 (May 25, 1990).
Genbank Accession # X14661, http://www.ncbi.nlm.nih.gov/nuccore/X14661 (Feb. 9, 1990).
Genbank Accession # X51447, http://www.ncbi.nlm.nih.gov/nuccore/X51447 (Sep. 9, 2004).
Genbank Accession # X52315, http://www.ncbi.nlm.nih.gov/nuccore/X52315 (Sep. 9, 2004).
Genbank Accession # X52527, http://www.ncbi.nlm.nih.gov/entrez/viewer.fcgi?db=nucleotide&val=16516 (Sep. 9, 2004).
Genbank Accession # X52528, http://www.ncbi.nlm.nih.gov/entrez/viewer.fcgi?db=nucleotide&val=16517(Sep. 9, 2004).
Genbank Accession # X52529, http://www.ncbi.nlm.nih.gov/entrez/viewer.fcgi?db=nucleotide&val=16518 (Sep. 9, 2004).
Genbank Accession # X52630, http://www.ncbi.nlm.nih.gov/entrez/viewer.fcgi?db=nucleotide&val=17671 (Sep. 9, 2004).
Genbank Accession # X60506, http://www.ncbi.nlm.nih.gov/nuccore/X60506 (Nov. 15, 2007).
Genbank Accession # X63065, http://www.ncbi.nlm.nih.gov/nuccore/X63065 (Nov. 15, 2007).
Genbank Accession # X63066, http://www.ncbi.nlm.nih.gov/nuccore/X63066 (Nov. 15, 2007).
Genbank Accession # X72228, http://www.ncbi.nlm.nih.gov/entrez/viewer.fcgi?db=nucleotide&val=572514 (Jun. 19, 1995).
Genbank Accession # X72229, http://www.ncbi.nlm.nih.gov/entrez/viewer.fcgi?db=nucleotide&val=572515 (Jun. 19, 1995).
Genbank Accession # X79685, http://www.ncbi.nlm.nih.gov/nuccore/X79685 (Oct. 14, 1996).

(56) References Cited

OTHER PUBLICATIONS

Genbank Accession # X17301, http://www.ncbi.nlm.nih.gov/entrez/viewer.fcgi?db=nucleotide&val=21467 (May 11, 1995).
Genbank Accession # Z29641, http://www.ncbi.nlm.nih.gov/entrez/viewer.fcgi?db=nucleotide&val=473184 (Jan. 19, 1995).
Zie et al., *Expression of Arabidopisis MIRNA Genes* [1][w], 138 Plant Physiology 2145-2154 (2005).
ter Brake et al., *Silencing of HIV-1 with RNA Interference: A Multiple shRNA Approach*, 14(6) Molecular Therapy 883-892 (2006).
Grimm et al., *Fatality in mice due to oversaturation of cellular microRNA/short hairpin RNA pathways*, 441(25) Nature 537-541 (2006).
Zhao et al., *Transiently Expressed Short Hairpin RNA Targeting 126 kDa Protein of Tobacco Mosaic Virus Interferes with Virus Infection*, (38)1 Acta Biochimica Et Biophysica Sinica 22-28 (2006).
Henderson et al., *Dissecting Arabidopsis thaliana Dicer function in small RNA processing, gene silencing and DNA methylation patterning*, 38(6) Nature Genetics 721-725 (2006).
Chung et al., *Polycistronic RNA polymerase II expression vectors for RNA interference based on BIC/miR-155*, 34(7) Nucleic Acids Research 1-14 (2006).
Sui et al., *A DNA vector-based RNAi technology to suppress gene expression in mammalian cells*, 99(8) PNAS 5515-5520 (2002).
Mette et al., *Production of aberrant promoter transcripts contributes to methylation and silencing of unlinked homologous promoters in trans*, 18(1) The EMBO Journal 241-248 (1999).

\* cited by examiner

SEQUENCE LISTING

```
<160> NUMBER OF SEQ ID NOS: 1

<210> SEQ ID NO 1
<211> LENGTH: 21
<212> TYPE: DNA
<213> ORGANISM: Arabidopsis

<400> SEQUENCE: 1
ttataagttt catgaagatg a                                              21
```

GENE SILENCING METHODS

CROSS-REFERENCE TO RELATED APPLICATIONS

This application is a continuation of U.S. application Ser. No. 12/673,428 filed on Feb. 22, 2011 which is the national stage of Application PCT/AU2008/001180 filed on Aug. 14, 2008, and claims the benefit of U.S. Application 61/013,604 filed on Dec. 13, 2007 and EP application No. 07015956.1 filed on Aug. 14, 2007, each of which is incorporated herein by reference in their entireties.

FIELD OF THE INVENTION

The invention relates to the field of recombinant DNA technology, more particularly to the modification of the expression of nucleic acids eukaryotic organisms through the provision of inhibitory RNA molecules. Described are methods for modifying gene silencing in plants by providing to the eukaryotic organism more than one type of inhibitory RNA, whereby said different types of inhibitory RNA are processed through various gene silencing pathways. The invention may be applied in different fields, including the agriculture, aquaculture or medical field.

BACKGROUND ART

Gene silencing is a common phenomenon in eukaryotes, whereby the expression of particular genes is reduced or even abolished through a number of different mechanisms ranging from mRNA degradation (post transcriptional silencing) over repression of protein synthesis to chromatin remodeling (transcriptional silencing).

The gene-silencing phenomenon has been quickly adopted to engineer the expression of different target molecules. Initially, two predominant methods for the modulation of gene expression in eukaryotic organisms were known, which are referred to in the art as "antisense" downregulation or "sense" downregulation.

In the last decade, it has been demonstrated that the silencing efficiency could be greatly improved both on quantitative and qualitative level using chimeric constructs encoding RNA capable of forming a double stranded RNA by basepairing between the antisense and sense RNA nucleotide sequences respectively complementary and homologous to the target sequences. Such double stranded RNA (dsRNA) is also referred to as hairpin RNA (hpRNA).

The following references describe the use of such methods:

Fire et al., 1998 (Nature 391, 806-811) describe specific genetic interference by experimental introduction of double-stranded RNA in *Caenorhabditis elegans*.

WO 99/32619 provides a process of introducing an RNA into a living cell to inhibit gene expression of a target gene in that cell. The process may be practiced ex vivo or in vivo. The RNA has a region with double-stranded structure. Inhibition is sequence-specific in that the nucleotide sequences of the duplex region of the RNA and or a portion of the target gene are identical.

Waterhouse et al. 1998 (Proc. Natl. Acad. Sci. USA 95: 13959-13964) describe that virus resistance and gene silencing in plants can be induced by simultaneous expression of sense and anti-sense RNA. The sense and antisense RNA may be located in one transcript that has self-complementarity.

Hamilton et al. 1998 (Plant J. 15: 737-746) describe that a transgene with repeated DNA, i.e., inverted copies of its 5' untranslated region, causes high frequency, post-transcriptional suppression of ACC-oxidase expression in tomato.

WO 98/53083 describes constructs and methods for enhancing the inhibition of a target gene within an organism which involve inserting into the gene silencing vector an inverted repeat sequence of all or part of a polynucleotide region within the vector.

WO 99/53050 provides methods and means for reducing the phenotypic expression of a nucleic acid of interest in eukaryotic cells, particularly in plant cells, by introducing chimeric genes encoding sense and antisense RNA molecules directed towards the target nucleic acid. These molecules are capable of forming a double stranded RNA region by base-pairing between the regions with the sense and antisense nucleotide sequence or by introducing the RNA molecules themselves. Preferably, the RNA molecules comprise simultaneously both sense and antisense nucleotide sequences.

WO 99/49029 relates generally to a method of modifying gene expression and to synthetic genes for modifying endogenous gene expression in a cell, tissue or organ of a transgenic organism, in particular to a transgenic animal or plant. Synthetic genes and genetic constructs, capable of forming a dsRNA which are capable of repressing, delaying or otherwise reducing the expression of an endogenous gene or a target gene in an organism when introduced thereto are also provided.

WO 99/61631 relates to methods to alter the expression of a target gene in a plant using sense and antisense RNA fragments of the gene. The sense and antisense RNA fragments are capable of pairing and forming a double-stranded RNA molecule, thereby altering the expression of the gene. The present invention also relates to plants, their progeny and seeds thereof obtained using these methods.

WO 00/01846 provides a method of identifying DNA responsible for conferring a particular phenotype in a cell which method comprises a) constructing a cDNA or genomic library of the DNA of the cell in a suitable vector in an orientation relative to (a) promoter(s) capable of initiating transcription of the cDNA or DNA to double stranded (ds) RNA upon binding of an appropriate transcription factor to the promoter(s); b) introducing the library into one or more of cells comprising the transcription factor, and c) identifying and isolating a particular phenotype of a cell comprising the library and identifying the DNA or cDNA fragment from the library responsible for conferring the phenotype. Using this technique, it is also possible to assign function to a known DNA sequence by a) identifying homologues of the DNA sequence in a cell, b) isolating the relevant DNA homologus(s) or a fragment thereof from the cell, c) cloning the homologue or fragment thereof into an appropriate vector in an orientation relative to a suitable promoter capable of initiating transcription of dsRNA from said DNA homologue or fragment upon binding of an appropriate transcription factor to the promoter and d) introducing the vector into the cell from step a) comprising the transcription factor.

WO 00/44914 also describes composition and methods for in vivo and in vitro attenuation of gene expression using double stranded RNA, particularly in zebrafish.

WO 00/49035 discloses a method for silencing the expression of an endogenous gene in a cell, the method involving overexpressing in the cell a nucleic acid molecule of the endogenous gene and an antisense molecule including a nucleic acid molecule complementary to the nucleic acid molecule of the endogenous gene, wherein the overexpression of the nucleic acid molecule of the endogenous gene and the antisense molecule in the cell silences the expression of the endogenous gene.

Smith et al., 2000 (Nature 407: 319-320) as well as WO 99/53050 described that intron containing dsRNA further increased the efficiency of silencing. Intron containing hairpin RNA is often also referred to as ihpRNA.

Although gene silencing was initially thought of as a consequence of the introduction of aberrant RNA molecules, such as upon the introduction of transgenes (transcribed to antisense sense or double stranded RNA molecules) it has recently become clear that these phenomena are not just experimental artifacts. RNA mediated gene silencing in eukaryotes appears to play an important role in diverse biological processes, such as spatial and temporal regulation of development, heterochromatin formation and antiviral defense.

All eukaryotes possess a mechanism that generates small RNAs which are then used to regulate gene expression at the transcriptional or post-transcriptional level. Various double stranded RNA substrates are processed into small, 21-24 nucleotide long RNA molecules through the action of specific ribonucleases (Dicer or Dicer-Like (DCL) proteins). Dedicated dsRNA binding (DRB) proteins associate with DCL proteint to optimize processing of their various dsRNA substrates into specifically sized small RNAs. These small RNAs serve as guide molecules incorporated into protein complexes (RNA-induced silencing complexes (RISC)) which further contain one member of the conserved Argonaute protein (AGO) family, which lead to the various effects achieved through gene silencing. Plants such as Arabidopsis have a broad spectrum of endogenous RNA silencing pathways owing to the presence of several specialized DCL proteins (four in Arabidopsis) and distinct AGO paralogs (ten in Arabidopsis).

Small RNAs involved in repression of gene expression in eukaryotes through sequence specific interactions with RNA or DNA are generally subdivided in two classes: microRNAs (miRNAs) and small interfering RNAs (siRNAs). These classes of small RNA molecules are distinguished by the structure of their precursors and by their targets. miRNAs are cleaved from the short, imperfectly paired stem of a much larger foldback transcript and regulate the expression of transcripts to which they may have limited similarity. siRNAs arise from a long double stranded RNA (dsRNA) and typically direct the cleavage of transcripts to which they are completely complementary, including the transcript from which they are derived (Yoshikawa et al., 2005, Genes & Development, 19: 2164-2175).

The number of Dicer family members varies greatly among organisms. In humans and C. elegans there is only one Dicer. In Drosophila, Dicer-1 and Dicer-2 are both required for small interfering RNA directed mRNA cleavage, whereas Dicer-1 but not Dicer-2 is essential for microRNA directed repression (Lee et al., 2004 Cell 75:843-854, Pham et al., 2004 Cell 117: 83-94).

Plants, such as Arabidopsis, appear to have at least four Dicer-like (DCL) proteins and it has been suggested in the scientific literature that these DCLs are functionally specialized (Qi et al., 2005 Molecular Cell, 19, 421-428)

DCL1 processes miRNAs from partially double-stranded stem-loop precursor RNAs transcribed from MIR genes (Kurihara and Watanabe, 2004, Proc. Natl. Acad. Sci. USA 101: 12753-12758).

DCL3 processes endogenous repeat and intergenic-region-derived siRNAs that depend on RNA-dependent RNA polymerase 2 and is involved in the accumulation of the 24nt siRNAs implicated in DNA and histone methylation (Xie et al., 2004, PLosBiology, 2004, 2, 642-652).

DCL2 appears to function in the antiviral silencing response for some, but not all plant-viruses ((Xie et al., 2004, PLosBiology, 2004, 2, 642-652).

Several publications have ascribed a role to DCL4 in the production of trans-acting siRNAs (ta-siRNAs). ta-siRNAs are a special class of endogenous siRNAs encoded by three known families of genes, designated TAS1, TAS2 and TAS3 in Arabidopsis thaliana. The biogenesis pathway for ta-siRNAs involves site-specific cleavage of primary transcripts guided by a miRNA. The processed transcript is then converted to dsRNA through the activities of RDR6 and SGS3. DCL4 activity then catalyzes the conversion of the dsRNA into siRNA duplex formation in 21-nt increments (Xie et al. 2005, Proc. Natl. Acad. Sci. USA 102, 12984-12989; Yoshikawa et al., 2005, Genes & Development, 19: 2164-2175; Gasciolli et al., 2005 Current Biology, 15, 1494-1500). As indicated in Xie et al. 2005 (supra) whether DCL4 is necessary for transgene and antiviral silencing remains to be determined.

Dunoyer et al. 2005 (Nature Genetics, 37 (12) pp 1356 to 1360) describe that DCL4 is required for RNA interference and produces the 21-nucleotide small interfering RNA component of the plant cell-to-cell silencing signal.

Dunoyer et al. 2007 (Nature Genetics 39 pp 848-856) summarizes the different pathways in Arabidopsis as follows: DCL1, together with the DRB protein HYL1, catalyzes release of miRNAs from imperfect fold-back precursor transcripts. Generally, miRNA-loaded AGO1 then promotes cleavage of cellular transcripts carrying miRNA target sequences 8. DCL3 produces 24-nt DNA repeat-associated siRNAs that guide heterochromatin formation by recruiting AGO4 and/or AGO6. DCL4, together with DRB4, generates 21-nt trans-acting siRNAs (tasiRNAs) that require AGO1 or AGO7 functions to mediate posttranscriptional silencing of genes controlling heteroblasty and leaf polarity. Finally, DCL2 produces natural antisense transcript siRNAs orchestrating stress responses 16.

Unpublished PCT application PCT/AU07/000583 describes the modulation of and demonstrates the involvement of DCL4 in the processing of long hairpin RNA molecules into interfering RNA components that ultimately effect gene-silencing.

Although RNAi mediated gene silencing has become an accepted research tool, as well as a tool for developing particular traits, there are incidental reports raising questions on the long-term stability of gene-silencing under particular conditions, or over the life-time of several generations, particularly in plant cells and plants. E.g. Szittya et al. 2003 (EMBO Journal 22, pp 633 to 640) reported that low temperature inhibits RNA silencing-mediated defence by the control of siRNA generation. Karmeda et al. 2004 report a temperature-sensitive gene silencing by an expressed inverted repeat in Drosophila (Biochem. Biophys. Res. Comm. 315, 599-602.) Niu et al. 2006 (Nature Biotechnology 24, 1420-1428) describe that viral infection systems by TYMV symptoms on Arabidopsis plants were more severe at 15° C. than at 24° C. and that transgenic plants comprising microRNA directed to downregulate the virus expression exhibited a stable amiRNA-mediated specific virus resistance maintained at 15° C.

In addition, some applications of RNAi, particularly as a trait development tool, require a severe downregulation of the target gene, preferably even the almost complete or complete downregulation for all practical means and purposes of the target gene function.

Applying RNAi to different target genes using different chimeric genes or RNA molecules which are processed via the same siRNA molecule producing pathway may lead to a saturation of such pathways.

Accordingly, described hereinafter in the different embodiments, examples and claims are methods and means for gene silencing that address the above mentioned problems, by providing and using at least two inhibitory RNA molecules or genes encoding such RNA molecules directed to the same target nucleic acid, whereby the inhibitory RNA molecules result in gene silencing through two or more separate pathways processing the RNAi into siRNA molecules, usually mediated by different Dicer proteins or Dicer like proteins (optionally in combination with different dsRNA binding proteins and/or members of the Argonaute family) and ultimately leading to gene silencing. To alleviate the problem of saturation of RNAi processing pathways methods and means are described providing and using at least two inhibitory RNA molecules or genes encoding such RNA molecules directed to different target nucleic acids, whereby the inhibitory RNA molecules result in gene silencing through two or more separate pathways processing the RNAi into siRNA molecules.

SUMMARY OF THE INVENTION

In one embodiment, the invention provides a method to reduce the expression of a target nucleic acid in a eukaryotic cell or organism, such as a plant cell or plant or an animal cell or non-human animal, comprising the step of introducing at least two inhibitory RNA molecules capable of reducing the expression of one target nucleic acid present in the eukaryotic cell, wherein the inhibitory RNA molecules are processed into oligonucleotides of 21 to 24 nucleotides in length via different RNAi molecule processing pathways, e.g. by cleavage into oligonucleotides of 21 to 24 nucleotides in length predominantly via separate dicer proteins or separate Dicerlike proteins.

In another embodiment, the invention provides a method to reduce the expression of first and second target nucleic acids in a eukaryotic cell or organism comprising the step of introducing a combination of at least two inhibitory RNA molecules, wherein one of the inhibitory RNA molecules is capable of reducing the expression of the first target nucleic acid in the eukaryotic cell or organism and the other of the inhibitory RNA molecules is capable of reducing the expression of the second target nucleic acid in said eukaryotic cell or organism, and wherein the inhibitory RNA molecules are processed into oligonucleotides of 21 to 24 nucleotides in length predominantly via different RNAi molecule processing pathways in the cell or organism.

In one embodiment of the invention, one of the inhibitory RNA molecules is predominantly cleaved via DCL1 or an RNAse with similar function and specificity and the other of the inhibitory RNA molecules is predominantly cleaved via DCL4 or an RNAse with similar function and specificity.

In another embodiment of the invention, one of the inhibitory RNA molecules is predominantly cleaved via DCL3 or an RNAse with similar function and specificity and the other of the inhibitory RNA molecules is predominantly cleaved via DCL4 or an RNAse with similar function and specificity.

Other combinations are also provided such as
a) one of the inhibitory RNA molecules is predominantly cleaved via DCL1 or an RNAse with similar function and specificity and the other of the inhibitory RNA molecules is predominantly cleaved via DCL2 or an RNAse with similar function and specificity;
b) one of the inhibitory RNA molecules is predominantly cleaved via DCL1 or an RNAse with similar function and specificity and the other of the inhibitory RNA molecules is predominantly cleaved via DCL3 or an RNAse with similar function and specificity;
c) one of the inhibitory RNA molecules is predominantly cleaved via DCL2 or an RNAse with similar function and specificity and the other of the inhibitory RNA molecules is predominantly cleaved via DCL3 or an RNAse with similar function and specificity; or
d) one of the inhibitory RNA molecules is predominantly cleaved via DCL2 or an RNAse with similar function and specificity and the other of the inhibitory RNA molecules is predominantly cleaved via DCL4 or an RNAse with similar function and specificity.

In yet another embodiment of the invention, a method is provided to reduce the expression of a target nucleic acid in a eukaryotic cell or organism, such as a plant cell or plant or an animal cell or non-human animal, comprising the step of introducing at least two inhibitory RNA molecules capable of reducing the expression of one target nucleic acid present in the eukaryotic cell, wherein one of the inhibitory RNA molecules is a miRNA molecule, a pre-microRNA molecule or a pri-mRNA molecule capable of reducing the expression of the target nucleic acid, and wherein the other inhibitory RNA molecule is a double stranded RNA molecule comprising a complementary or essentially complementary first and second RNA region, the first RNA region comprising at least 19 consecutive nucleotides selected from the nucleotide sequence of the target nucleic acid and the second RNA region comprising at least 19 consecutive nucleotides selected from the complement of the nucleotide sequence of the target nucleic acid. In another embodiment, the mentioned first inhibitory RNA molecule may comprise at least 19 consecutive nucleotides from a promoter region of the target nucleic acid molecule, and the second inhibitory RNA molecule may comprise at least 19 consecutive nucleotides from the region of the target nucleic acid molecule which is transcribed into a RNA molecule.

In still another embodiment according to the invention, the inhibitory RNA molecules are transcribed from inhibitory RNA encoding genes introduced in the eukaryotic cell. In a particular embodiment of the invention, the inhibitory RNA molecules may transcribed from an inhibitory RNA encoding gene under control of a promoter recognized by RNA polymerase II and the other inhibitory RNA may be transcribed from an inhibitory RNA encoding gene under control of a promoter recognized by RNA polymerase III.

The target nucleic acid may be a viral nucleic acid or a gene or transcribed region thereof or it may be a transgene or it may be an endogene.

The expression of the target nucleic acid achieved by the method according to the invention may be more reduced or more stable or less sensitive to external factors than the reduction of expression of the target nucleic acid achieved by any of the inhibitory RNA molecules separately in the eukaryotic organism.

It is another objective of the invention to provide a eukaryotic cell, such as a plant or animal cell, comprising at least two inhibitory RNA molecules capable of reducing the expression of one target nucleic acid present in the eukaryotic cell, wherein the inhibitory RNA molecules are processed into oligonucleotides of 21 to 24 nucleotides in length via different RNAi molecule processing pathways.

Also provided by the invention are non-human eukaryotic organisms consisting essentially or completely of the above mentioned cells.

In yet another embodiment, the invention provides a composition of matter comprising at least two inhibitory RNA molecules capable of reducing the expression of one target nucleic acid present in the eukaryotic cell, wherein the inhibitory RNA molecules are processed into oligonucleotides of 21 to 24 nucleotides in length via different RNAi molecule processing pathways.

The invention also provides a kit comprising at least two inhibitory RNA molecules capable of reducing the expression of one target nucleic acid present in the eukaryotic cell, wherein the inhibitory RNA molecules are processed into oligonucleotides of 21 to 24 nucleotides in length via different RNAi molecule processing pathways, as a combined preparation for simultaneous, separate or sequential use in reduction of the expression of a target nucleic acid in a eukaryotic organism.

Also provided by the invention are composition of matter comprising at least two inhibitory RNA molecules as herein described, and the use thereof as a medicament.

Panel B: Silencing of PDS expression in different transgenic lines comprising either CaMV35S driven PDS hp42 transgenes (35S-X; top of each plate), AtU6 driven PDS hp42 transgenes (U6-XX; bottom of each plant) and plant lines comprising both transgenes (35S-X×U6-XX; middle of each plate).

Figure 2:
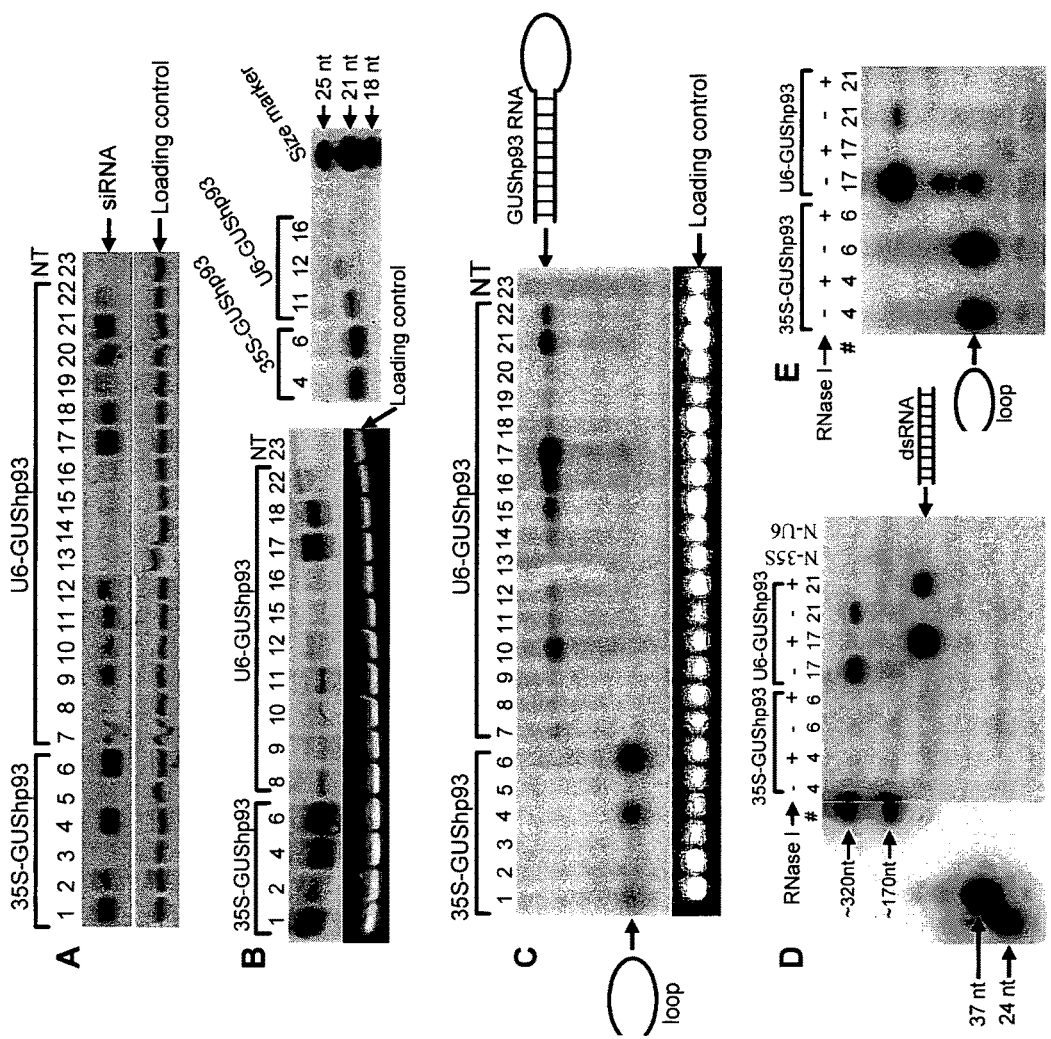

FIG. 2. Northern blot analysis showing differential processing of hpRNA derived from 35S-GUShp93 and U6-GUShp93 transgenes in *Arabidopsis*. Panel A. Detection of siRNAs. Note the overall difference in siRNA size patterns between the 35S and the U6 lines. Panel B. Better separations of siRNAs. Subsets of the small RNA samples in A were separated in either 15% (left panel) or 18% (right) polyacrylamide gel and hybridized with the same probe as for A. Note that siRNAs from the 35S lines are predominantly 21 nt in size whereas siRNAs from the U6 lines are 22 and/or 24 nt in size. Panel C. Northern blot analysis of intermediate RNAs in 35S-GUShp93 and U6-GUShp93 *Arabidopsis* plants. Total small RNAs was separated in 5% formaldehyde-agarose (NuSieve 3:1) gels, and hybridized with $^{32}$P-labelled full-length antisense GUS RNA (top panel). Panel D. Four of the total small RNA samples shown in C (#4, #6, #17 and #21) were untreated (−) or treated (+) with RNase I, separated in 5% formaldehyde-agarose (NuSieve 3:1) gel, and hybridized with $^{32}$P-labelled sense RNA corresponding to the stem and loop of GUShp93 RNA (i.e. nt. 512-697 of GUS ORF), which should detect the full-length RNA and the dsRNA stem, but not the loop fragment, of the GUShp93 transcript. N-35S and N-U6 are nuclear RNA preparations from the pooled 35S-GUShp93 and U6-GUShp93 plants, respectively. Panel E. The same four samples were untreated (−) or treated (+) with RNase I, separated in 5% formaldehyde-agarose (NuSieve 3:1) gel, and hybridized with $^{32}$P-labelled antisense RNA corresponding to the loop of GUShp93 RNA (i.e. nt.605-697 of GUS ORF). Note that the 35S-GUShp93-derived RNA intermediate hybridized only with the antisense probes (C and E) but not with the sense probe (D), indicating the hybridizing band was the loop fragment.

Figure 3:
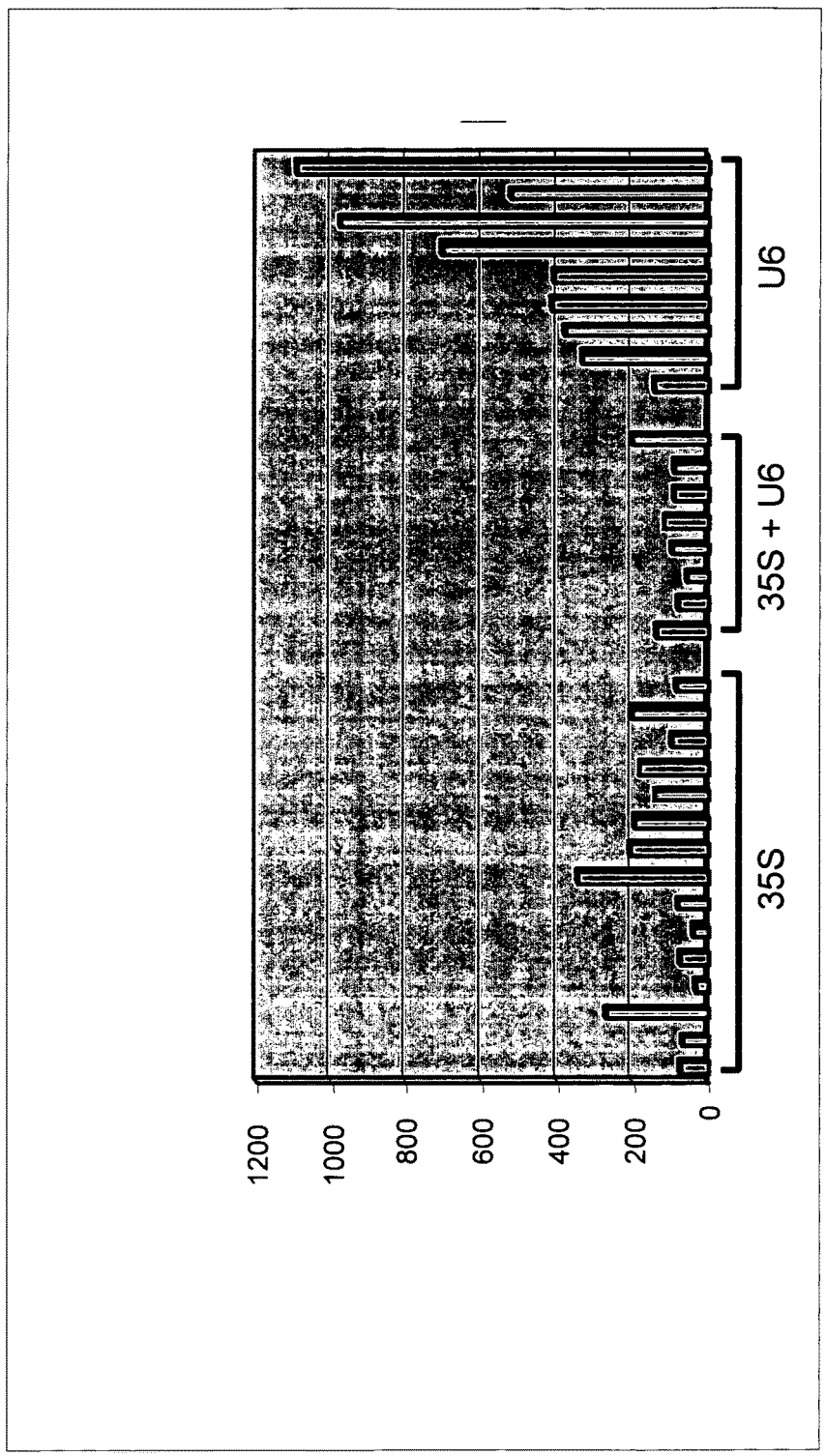

FIG. 3 Analysis of GUS expression in different transgenic lines containing either 35S-GUShp93 chimeric gene or AtU6hp93 chimeric gene or both.

Figure 4:
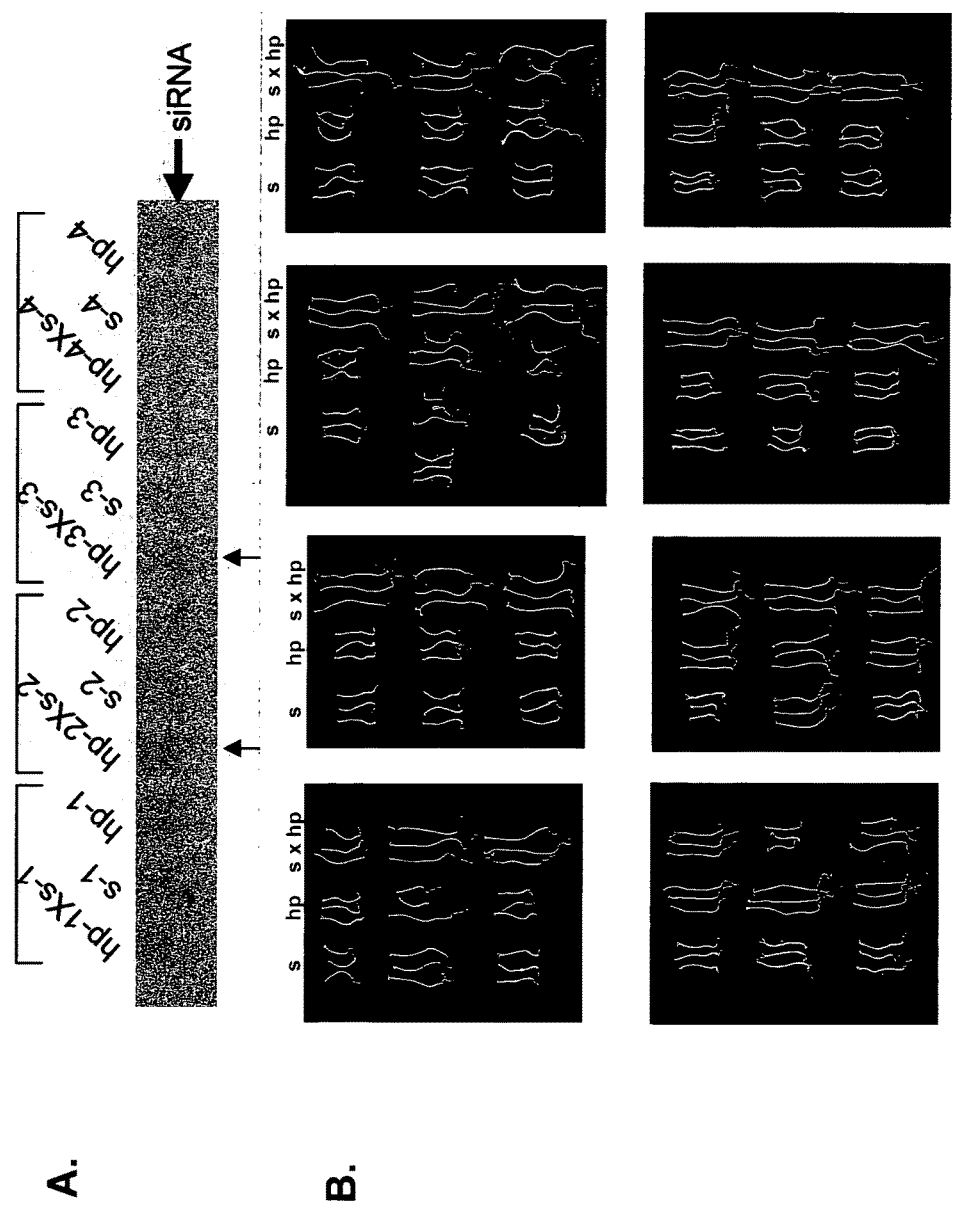

FIG. 4. Panel A: Northern analysis of short RNA molecules in transgenic lines containing either a hpRNA directed to the promoter and transcribed region of EIN2 (hp); a sense RNA directed to the promoter of EIN2 (s) or transgenic lines comprising both types of transgenes (hp×s).

Panel B: EIN2 silencing in different transgenic lines comprising a transgene encoding a sense inhibitory RNA directed against the promoter region of the EIN2 endogenous gene (s); in transgenic lines comprising a transgene encoding a double stranded inhibitory RNA against the promoter region of the EIN2 endogenous gene, as well as the 5' UTR of the mRNA encoding region of the EIN2 endogenous gene (hp); and in lines comprising both transgenes (s×hp). Seeds are sown on medium containing ACC and grown in the dark. The more elongated the hypocotyls, the stronger the silencing of the expression of the EIN2 gene.

DETAILED DESCRIPTION OF DIFFERENT EMBODIMENTS OF THE INVENTION

The current invention is based on the demonstration by the inventors that eukaryotic cells, such as plant cells, exhibit a more pronounced and more stable reduction of the expression of a particular target nucleic acid when provided with at least two inhibitory RNA molecules directed to the particular target nucleic acid, each of the inhibitory RNA molecules exerting its ultimate effect through a different gene silencing pathway, than the reduction in target nucleic acid expression observed in eukaryotic cells provided with only one of the inhibitory molecules.

In particular, it was demonstrated that gene-silencing achieved by chimeric genes encoding a double stranded RNA molecule (particularly a hpRNA) in plant cells was more enhanced when a combination was provided of a chimeric gene encoding a hpRNA under control of a promoter recognized by RNA polymerase II and a chimeric gene encoding a hpRNA under control of a promoter recognized by RNA polymerase III, particularly type 3 promoter. Similarly, an enhanced reduction in the expression of the target nucleic acid could be observed by the provision of two separate chimeric genes, one of the chimeric gene encoding an inhibitory RNA (so-called co-suppression or sense gene silencing construct) directed towards the promoter region, the other chimeric gene encoding an inhibitory RNA (hpRNA) directed also to the transcribed region of the target nucleic acid. Additionally an enhanced reduction of expression is expected from the combination of a microRNA encoding chimeric gene and an hpRNA encoding gene. It is also expected that such combinations will be effective in other eukaryotic cells such as animal cells.

Accordingly, the invention provides a method to reduce the expression of a target nucleic acid in a eukaryotic cell or organism whereby at least two inhibitory RNA molecules capable of reducing the expression of one target nucleic acid present in the eukaryotic cell are introduced into the eukaryotic cell and whereby the inhibitory RNA molecules are processed into oligonucleotides of 21 to 24 nucleotides in length via different RNAi molecule processing pathways. Such methods unexpectedly results in increased reduction of the expression of the target nucleic acid. Moreover, since the inhibitory RNA molecules result in the ultimate gene-silencing effect through different pathways, the methods are less prone to external stimuli that interfere with one of the processing pathways, but not with the other.

As used herein "gene-silencing effect" refers to the "reduction of expression of a target nucleic acid" in a host cell, preferably a plant cell, which can be achieved by introduction of a silencing RNA. "Expression of a target nucleic acid" refers to transcription of the nucleic acid in the cell, and the reduced expression may be observed or measured by a reduced level of production or accumulation of the transcript or a processed product, for example of an mRNA, or of a translation product of the mRNA. The transcript may or may not be processed, for example by removal of introns, and it may or may not be translated; "expression" encompasses transcription with or without such processes. The reduction of expression may be the result of reduction of transcription, including via methylation of chromatin remodeling, or post-transcriptional modification of the RNA molecules, including via RNA degradation, or both. Gene-silencing should not necessarily be interpreted as an abolishing of the expression of the target nucleic acid or gene. It is sufficient that the level expression of the target nucleic acid in the presence of the silencing RNA is lower that in the absence thereof. The level of expression may be reduced by at least about 10% or at least about 15% or at least about 20% or at least about 25% or at least about 30% or at least about 35% or at least about 40% or at least about 45% or at least about 50% or at least about 55% or at least about 60% or at least about 65% or at least about 70% or at least about 75% or at least about 80% or at least about 85% or at least about 90% or at least about 95% or at least about 100%. As used herein, unless stated to the contrary, the phrase "about" refers to any reasonable range in light of the value in question. In a preferred embodiment, the term "about" refers to +/−1% of the specified value. As used herein, "to a greater extent" refers to an increase in effect of at least 10% relative to the reference. Target nucleic acids may include endogenous genes, transgenes or viral genes or genes introduced by viral vectors. Target nucleic acid may further include genes which are stably introduced in the host's cell genome, preferably the host cell's nuclear genome.

As used herein, "silencing RNA" or "silencing RNA molecule" also referred to herein as "inhibitory RNA" or "inhibitory RNA molecule" indicates any RNA molecule which upon introduction into a host cell, preferably a plant cell, reduces the expression of a target gene, particularly through transcriptional and/or post-transcriptional silencing. Such silencing RNA may e.g. be so-called "antisense RNA", whereby the RNA molecule comprises a sequence of at least 20 consecutive nucleotides having at least 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having at least 95% sequence identity to the sequence of the target nucleic acid. Sense RNA may also be directed to regulatory sequences of target genes, including the promoter sequences and transcription termination and polyadenylation signals.

The mentioned sense or antisense RNA may of course be longer and be about 30 nt, about 50 nt, about 100 nt, about 200 nt, about 300 nt, about 500 nt, about 1000 nt, about 2000 nt or even about 5000 nt or larger in length, each having an overall sequence identity of respectively about 40%, 50%, 60%, 70%, 80%, 90% or 100% with the nucleotide sequence of the target nucleic acid (or its complement) The longer the sequence, the less stringent the requirement for the overall sequence identity. However, the longer sense or antisense RNA molecules with less overall sequence identity should at least comprise 20 consecutive nucleotides having at least 95% sequence identity to the sequence of the target nucleic acid or its complement and may comprise at least 20 consecutive nucleotides having 100% sequence identity to the sequence of the target nucleic acid or its complement. The length of the sense or antisense RNA may be between any combination of the above figures. In an embodiment, preferred for use in animal cells particularly mammalian cells the length of the sense or antisense RNA is between 20 and 30 nucleotides. In embodiments, the length of the sense or antisense RNA is 21, 22, 23, 24, 25, 26, 27, 28, or 29 nucleotides. Where the silencing RNA includes both sense and antisense RNA, the length of each may independently be any figure as mentioned above. In a preferred embodiment, the length of the sense and antisense RNAs are the same or differ by up to 10% or 20%, not more.

The two inhibitory RNA molecules may target the same region, overlapping regions, or preferably non-overlapping regions of the target nucleic acid. As used herein, "overlapping" means that the two regions overlap with at least 2 consecutive nucleotides in common. In a more preferred embodiment, particularly for use in animal cells such as mammalian cells, one of the two inhibitory RNA molecules is a short hairpin RNA which may be polyadenylated but is preferably unpolyadenylated, having a sense nucleotide sequence of 20-30 consecutive nucleotides at least 95% identical to the first region of 20-30 nucleotides of the target gene and an antisense nucleotide sequence of 20-30 consecutive nucleotides at least 95% identical to the complement of the first region of the target gene, the sense and antisense sequences being covalently joined by a spacer region of 3-20 nucleotides, and the second of the two inhibitory RNA molecules is a miRNA molecule having an antisense nucleotide sequence of 20-30 consecutive nucleotides, preferably 20-25 consecutive nucleotides, at least 95% identical to the complement of a second region of 20-30 or 20-25 nucleotides of the target gene but not having a sense nucleotide sequence of at least 20 consecutive nucleotides at least 95% identical to the second region of the target gene. The miRNA molecule may or may not have a sense nucleotide sequence of 20-30 consecutive nucleotides which is 60-95% identical in sequence to the second region of the target gene. The first and second regions of the target gene are preferably not the same, and more preferably non-overlapping. Preferably, the short hairpin RNA is expressed from a chimeric gene having an RNA polymerase III (RNA Pol III) promoter and the miRNA molecule is transcribed from a chimeric gene having an RNA Pol II promoter as a precursor RNA (pri-miRNA or pre-microRNA) which is subsequently processed in the cell.

Other silencing RNA may be "unpolyadenylated RNA" comprising at least 20 consecutive nucleotides having at least 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 or WO2005/026356 (both documents herein incorporated by reference) comprising at least 20 consecutive nucleotides having at least 95% sequence identity to the sequence of the target nucleic acid or the complement thereof, and further comprising a largely-double stranded region as described in WO03/076619 or WO2005/026356 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA molecules could also comprise so-called microRNA or synthetic or artificial microRNA molecules or their precursors, as described e.g. in Schwab et al. 2006, Plant Cell 18(5):1121-1133.

Silencing RNA can be introduced directly into the host cell, or indirectly through transcription of a "gene-silencing chimeric gene" introduced into the host cell. The gene-silencing chimeric gene may be introduced stably into the host cell's (such as a plant cell) genome, preferably nuclear genome, or it may be introduced transiently.

All silencing RNA as herein defined has an intermediate phase wherein the silencing RNA molecule comprises a double stranded RNA region. A "double-stranded RNA region" as used herein has two RNA strands which are hybridized by basepairing. The two strands may be separate strands (not covalently joined) or may be joined covalently via a spacer or loop region as parts of a single self-complementary RNA. "Basepairing" in this context includes G:U basepairs as well as standard Watson-Crick basepairing. Either the single stranded RNA is partially or completely converted into a double stranded RNA through the action of e.g. a RNA dependent RNA polymerase, or the inhibitory RNA molecule introduced or transcribed is itself capable of forming such double stranded RNA region. If the eukaryotic organism contains more than one dicer or dicerlike protein (such as e.g. in plant cells) the different dicers or dicerlike proteins may have a preference for the double stranded RNA substrates and may also differ in the length of the short interfering RNAs produced and it is this difference in processing by different Dicer or dicer like proteins or through different activities of the Dicer or dicer-like proteins that is referred as "different RNAi molecule processing pathways". Such difference in activity and specificity for a particular dsRNA substrate may further be extended by associated with different dedicated doublestranded RNA binding proteins as well as by the incorporation of the generated small interfering RNA molecules into different RISC complexes comprising different Argonaute like proteins.

As used herein, a "Dicer protein" is a protein having ribonuclease activity which is involved in the processing of double stranded RNA molecules into short interfering RNA (siRNA). The ribonuclease activity is so-called ribonuclease III activity, which predominantly or preferentially cleaves double stranded RNA substrates rather than single-stranded RNA regions thereby targeting the double stranded portion of the RNA molecule. As used herein, the term "predominantly" means at least 51% up to and including 100%, or having greater activity of one type than another. The term Dicer includes Dicer-like (DCL) proteins. Dicer proteins are preferentially involved in processing the doublestranded RNA substrates into siRNA molecules of about 21 to 24 nucleotides in length. As used herein a "plant dicer" or plant "dicer-like" protein is a protein having ribonuclease activity on double stranded RNA substrates (ribonuclease III activity) which is characterized by the presence of at least the following domains: a DExD or DExH domain (DEAD/DEAH domain), a Helicase-C domain, preferably a Duf283 domain which may be absent, a PAZ domain, two RNAse III domains and at least one and preferably 2 dsRB domains.

Helicase C: The domain, which defines this group of proteins is found in a wide variety of helicases and helicase related proteins. It may be that this is not an autonomously folding unit, but an integral part of the helicase (PF00271; IPR001650)

PAZ domain: This domain is named after the proteins Piwi Argonaut and Zwille. It is also found in the CAF protein from *Arabidopsis thaliana*. The function of the domain is unknown but has been found in the middle region of a number of members of the Argonaute protein family, which also contain the Piwi domain in their C-terminal region. Several members of this family have been implicated in the development and maintenance of stem cells through the RNA-mediated gene-quelling mechanisms associated with the protein Dicer. (PF02170; IPR003100)

Duf283: This putative domain is found in members of the Dicer protein family. This protein is a dsRNA nuclease that is involved in RNAi and related processes. This domain of about 100 amino acids has no known function, but does contain 3 possible zinc ligands.(PF03368, IPR005034).

DExD: Members of this family include the DEAD and DEAH box helicases. Helicases are involved in unwinding nucleic acids. The DEAD box helicases are involved in various aspects of RNA metabolism, including nuclear transcription, pre mRNA splicing, ribosome biogenesis, nucleo-cytoplasmic transport, translation, RNA decay and organellar gene expression (PF00270, IPR011545).

RNAse III: signature of the ribonuclease III proteins (PF00636, IPR000999)

DsRB (Double stranded RNA binding motif): Sequences gathered for seed by HMM_iterative_training Putative motif shared by proteins that bind to dsRNA. At least some DSRM proteins seem to bind to specific RNA targets. Exemplified by Staufen, which is involved in localisation of at least five different mRNAs in the early *Drosophila* embryo. Also by interferon-induced protein kinase in humans, which is part of the cellular response to dsRNA (PF00035, IPR001159).

These domains can easily be recognized by computer based searches using e.g. PROSITE profiles PD0050821 (PAZ domain), PD0000448 (RNase III domain), PD0050137 (dsRB domain) and PD0000039 (DExD/DexH domain) (PROSITE is available at www.expasy.ch/prosite). Alternatively, the BLOCKS database and algorithm (blocks-.fhcrc.org) may be used to identify PAZ(IPB003100) or DUF283(IPB005034) domains. Other databases and algorithms are also available (pFAM: www.sanger.ac.uk/Software/Pfam/INTERPRO: www.ebi.ac.uk/interpro/; the above cited PF numbers refer to pFAM database and algorithm and IPR numbers to the INTERPRO database and algorithm).

Typically, in plants, a DCL2 protein will process double stranded RNA into short interfering RNA molecules of about 22 nucleotides, a DCL3 protein will process double stranded RNA into short interfering RNA molecules of about 24 nucleotides, and DCL4 will process double stranded RNA into short interfering RNA molecules of about 21 nucleotides. DCL1 is involved in the processing of microRNA's from pre-microRNA molecules. Without intending to limit the invention to a particular mode of action, it is generally thought that the 24 nucleotides long oligonucleotides mediate the methylation and chromatin modeling while the 21 and 22 long oligonucleotides typically mediate sequence specific RNA degradation (both in combination with other proteins and polypeptides).

The dicer-like proteins are well known in the art. Dicer-like 3 enzymes are those which encode a protein comprising an amino acid sequence of at least about 60% or at least about 65% or at least about 70% or at least about 75% or at least about 80% or at least about 85% or at least about 90% or at least about 95% sequence identity or being essentially identical with the proteins comprising an amino acid sequence available from databases with the following accession numbers: NP_189978.

Dicer-like 4 proteins are those which encode a protein comprising an amino acid sequence of at least about 60% or 65% or 70% or 75% or 80% or 85% or 90% or 95% sequence identity or being essentially identical with the proteins comprising an amino acid sequence of available from databases with the following accession numbers: AAZ80387; P84634.

Dicer-like 2 proteins are those which encode a protein comprising an amino acid sequence of at least about 60% or 65% or 70% or 75% or 80% or 85% or 90% or 95% sequence identity or being essentially identical with the proteins comprising an amino acid sequence of available from databases with the following accession numbers: NP_001078101.

Dicer-like 1 proteins are those which encode a protein comprising an amino acid sequence of at least about 60% or 65% or 70% or 75% or 80% or 85% or 90% or 95% sequence identity or being essentially identical with the proteins comprising an amino acid sequence available from databases e.g. with the following accession numbers: Q9SP32.

An enzymatic assay which can be used for detecting RNAse III enzymatic activity is described e.g; in Lamontagne et al., Mol Cell Biol. 2000 February; 20(4): 1104-1115. The resulting cleavage products can be further analyzed according to standard methods in the art for the generation of 21-24 nt siRNAs.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch 1970) The computer-assisted sequence alignment above, can be conveniently performed using standard software program such as GAP which is part of the Wisconsin Package Version 10.1 (Genetics Computer Group, Madision, Wis., USA) using the default scoring matrix with a gap creation penalty of 50 and a gap extension penalty of 3. Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are the to be essentially similar or have a certain degree of sequence identity with DNA sequences, thymine (T) in the DNA sequence is considered equal to uracil (U) in the RNA sequence. Thus when it is stated in this application that a sequence of 19 consecutive nucleotides has at least 94% sequence identity to a sequence of 19 nucleotides, this means that at least 18 of the 19 nucleotides of the first sequence are identical to 18 of the 19 nucleotides of the second sequence.

Thus, the invention provides methods for reducing the expression of a target nucleic acid in a plant cell or other eukaryotic cell (or plant or eukaryotic organism) by the introduction of at least two inhibitory RNA molecules capable of reducing the expression of one and the same target nucleic acid present in the eukaryotic cell whereby one of the inhibitory RNA molecules is predominantly cleaved via DCL1 or a similar RNAse, while the other of the inhibitory RNA molecules is predominantly cleaved via DCL4 or a similar RNAse. Without intending to limit the invention, such a method can be performed by introducing into one cell a microRNA targeted towards the nucleic acid of interest and a doublestranded hairpin RNA, particularly a longer hpRNA (comprising e.g. a double stranded RNA region of at least 50, 60, 90, 120, 150, 300 nucleotides) targeted towards the same nucleic acid of interest.

The invention also provides methods for reducing the expression of a target nucleic acid in a plant cell or other eukaryotic cell (or plant or eukaryotic organism) by the introduction of at least two inhibitory RNA molecules capable of reducing the expression of one and the same target nucleic acid present in the eukaryotic cell whereby one of the inhibitory RNA molecules is predominantly cleaved via DCL3 or a similar RNAse, while the other of the inhibitory RNA molecules is predominantly cleaved via DCL4 or a similar RNAse. Without intending to limit the invention, such a method can be performed by introducing into one cell an inhibitory RNA directed towards the regulatory regions of a target gene (such as the promoter region), while the other inhibitory RNA is directed towards the transcribed region of the target gene. In another way, such method can be performed by providing the cell with two chimeric genes encoding the inhibitory RNA, the expression of one chimeric gene being directed by a promoter recognized by a DNA dependent RNA polymerase II, while the expression of the other chimeric gene is directed by a promoter recognized by a DNA dependent RNA polymerase III, such a promoter of the subtype 3.

Similarly, the invention provides for other combinations of inhibitory RNA such as:
  One inhibitory RNA predominantly cleaved by DCL1 or a similar RNAse and one inhibitory RNA predominantly cleaved by DCL2 or similar RNAse;
  One inhibitory RNA predominantly cleaved by DCL1 or a similar RNAse and one inhibitory RNA predominantly cleaved by DCL3 or similar RNAse;
  One inhibitory RNA predominantly cleaved by DCL2 or a similar RNAse and one inhibitory RNA predominantly cleaved by DCL3 or similar RNAse; and One inhibitory RNA predominantly cleaved by DCL2 or a similar RNAse and one inhibitory RNA predominantly cleaved by DCL4 or similar RNAse.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

In one embodiment of the invention the promoter is a promoter recognized by RNA polymerase II. RNA PolII promoters include most commonly known promoters. In another embodiment of the invention the promoter is a promoter recognized by RNA polymerase III. As used herein "a promoter recognized by the DNA dependent RNA polymerase III" is a promoter which directs transcription of the associated DNA region through the polymerase action of RNA polymerase III. These include genes encoding 5S RNA, tRNA, 7SL RNA, U6 snRNA and a few other small stable RNAs, many involved in RNA processing. Most of the promoters used by Pol III require sequence elements downstream of +1, within the transcribed region. A minority of pol III templates however, lack any requirement for intragenic promoter elements. These are referred to as type 3 promoters. In other words, <<type 3 Pol III promoters>>, are those promoters which are recognized by RNA polymerase III and contain all cis-acting elements, interacting with the RNA polymerase III upstream of the region normally transcribed by RNA polymerase III. Such type 3 Pol III promoters can thus easily be combined in a chimeric gene with a heterologous region, the transcription of which is desired, such as the dsRNA coding regions of the current invention.

Typically, type 3 Pol III promoters contain a TATA box (located between −25 and −30 in Human U6 snRNA gene) and a Proximal Sequence element (PSE; located between −47 and −66 in Human U6 snRNA). They may also contain a Distal Sequence Element (DSE; located between −214 and −244 in Human U6 snRNA).

Type 3 Pol III promoters can be found e.g. associated with the genes encoding 7SL RNA, U3 snRNA and U6 snRNA. Such sequences have been isolated from *Arabidopsis*, rice and tomato and can be found in nucleotide sequence databases under the entries for the *A. thaliana* gene AT7SL-1 for 7SL RNA (X72228), *A. thaliana* gene AT7SL-2 for 7SL RNA (X72229), *A. thaliana* gene AT7SL-3 for 7SL RNA (AJ290403), *Humulus lupulus* H17SL-1 gene (AJ236706), *Humulus lupulus* H17SL-2 gene (AJ236704), *Humulus lupulus* H17SL-3 gene (AJ236705), *Humulus lupulus* H17SL-4 gene (AJ236703), *A. thaliana* U6-1 snRNA gene (X52527), *A. thaliana* U6-26 snRNA gene (X52528), *A. thaliana* U6-29 snRNA gene (X52529), *A. thaliana* U6-1 snRNA gene (X52527), *Zea mays* U3 snRNA gene (Z29641), *Solanum tuberosum* U6 snRNA gene (Z17301; X 60506; S83742), Tomato U6 smal nuclear RNA gene (X51447), *A. thaliana* U3C snRNA gene (X52630), *A. thaliana* U3B snRNA gene (X52629), *Oryza sativa* U3 snRNA promoter (X79685), Tomato U3 smal nuclear RNA gene (X14411), *Triticum aestivum* U3 snRNA gene (X63065), *Triticum aestivum* U6 snRNA gene (X63066).

It goes without saying that variant type 3 Pol III promoters may be isolated from other varieties of tomato, rice or *Arabidopsis*, or from other plant species without little experimentation. E.g. libraries of genomic clones from such plants may be isolated using U6 snRNA, U3 snRNA or 7SL RNA coding sequences (such as the coding sequences of any of the above mentioned sequences identified by their accession number and additionally the *Vicia faba* U6snRNA coding sequence (X04788), the maize DNA for U6 snRNA (X52315) or the maize DNA for 7SL RNA (X14661)) as a probe, and the upstream sequences, preferably the about 300 to 400 bp upstream of the transcribed regions may be isolated and used as type 3 Pol III promoters. Alternatively, PCR based techniques such as inverse-PCR or TAIL®-PCR may be used to isolate the genomic sequences including the promoter sequences adjacent to known transcribed regions. Moreover, any of the type 3 PolIII promoter sequences attached or of the above mentioned promoter sequences, identified by their accession numbers, may be used as probes under stringent hybridization conditions or as source of information to generate PCR primers to isolate the corresponding promoter sequences from other varieties or plant species.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

Although the type 3 Pol III promoters have no requirement for cis-acting elements located with the transcribed region, it is clear that sequences normally located downstream of the transcription initiation site may nevertheless be included in the chimeric constructs of the invention.

It has also been observed that type 3 Pol III promoters originally isolated from monocotyeldonous plants can be used to good effect in both dicotyledonous and monocotyleodous plant cells and plants, whereas type 3 Pol III promoters originally isolated from dicotyledonous plants can only be efficiently used in dicotyledonous plant cells and plants. Moreover, the most efficient gene silencing has been obtained when chimeric genes were used comprising a type 3 Pol III promoter derived from the same or closely related species.

Typically, terminator regions for PolIII polymerase mediated transcription constitute of an oligo dT stretch, a stretch of consecutive T-residues which comprises at least 4 T-residues, but obviously may contain more T-residues.

In one embodiment of the invention, the promoter is a constitutive promoter. In another embodiment of the invention, the promoter activity is enhanced by external or internal stimuli (inducible promoter), such as but not limited to hormones, chemical compounds, mechanical impulses, abiotic or biotic stress conditions. The activity of the promoter may also regulated in a temporal or spatial manner (tissue-specific promoters; developmentally regulated promoters).

In a particular embodiment of the invention, the promoter is a plant-expressible promoter. As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e. certain promoters of viral or bacterial origin such as the CaMV35S (Hapster et al., 1988 Mol. Gen. Genet. 212, 182-190), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996 The Plant Cell 8, 15-30), stem-specific promoters (Keller et al., 1988 EMBO J. 7: 3625-3633), leaf specific promoters (Hudspeth et al., 1989 Plant Mol Biol 12: 579-589), mesophyl-specific promoters (such as the light-inducible Rubisco promoters), root-specific promoters (Keller et al., 1989 Genes Devel. 3: 1639-1646), tuber-specific promoters (Keil et al., 1989 EMBO J. 8: 1323-1330), vascular tissue specific promoters (Peleman et al., 1989 Gene 84: 359-369), stamen-selective promoters (WO 89/10396, WO 92/13956), dehiscence zone specific promoters (WO 97/13865) and the like.

The invention also contemplates the use of artificial or man-made microRNA molecules in combination with an inhibitory RNA processed predominantly via an RNAi processing pathway different from the microRNA processing pathway. In plants, this refers to an RNAi processing pathway different from the RNAse III activity of Dicerlike 1. The generation of artificial microRNA molecules directed at a particular target nucleic acid is already quite established in the art.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur:
  A mismatch between the nucleotide at the 5' end of said miRNA and the corresponding nucleotide sequence in the target RNA molecule;
  A mismatch between any one of the nucleotides in position 1 to position 9 of said miRNA and the corresponding nucleotide sequence in the target RNA molecule;
  Three mismatches between any one of the nucleotides in position 12 to position 21 of said miRNA and the corresponding nucleotide sequence in the target RNA molecule provided that there are no more than two consecutive mismatches.
  No mismatch is allowed at positions 10 and 11 of the miRNA (all miRNA positions are indicated starting from the 5' end of the miRNA molecule).

A miRNA is processed from a "pre-miRNA" molecule by proteins, such as DCL proteins, present in any plant cell and loaded onto a RISC complex where it can guide the cleavage of the target RNA molecules.

Pre-microRNA molecules are usually processed from pri-microRNA molecules (primary transcripts). In animals, microRNA maturation is initiated by the Drosha-DGCR8 complex by precise cleavage of the stem loops that are embedded in primary transcripts. The single stranded RNA segments flanking the pre-microRNA are important for processing of the pri-miRNA into the premiRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Interestingly, it has been observed that some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA. In particular, it has been found that the transcription of a primary transcript comprising a pre-microRNA and other more or less complementary regions may interfere with the correct processing of the primary transcript into pre-microRNA and ultimately into the designed micro-RNA. Other pre-microRNA scaffolds, such as e.g. premicroRNA398, may be less prone to such incorrect processing. It is expected that the presence of one or more unstructured single stranded regions at a particular fixed location from the cleavage site of pre-miRNA molecule in an overall mostly double-stranded RNA region, influences the correct processing of the designed pre-miRNA molecules and contributes to the fact that e.g. processing of pre-miR398 derived scaffolds from the primary transcript is less prone to errors than e.g. processing of pre-miR171 derived scaffolds from primary transcripts.

It will be immediately clear to the skilled artisan that the presence of additional sequences may have an influence on the folding of the primary transcript RNA molecule into a secondary RNA structure and particularly on presence and location of bulges or single stranded RNA structures in otherwise doublestranded RNA stem (sub)structures. The location of single-stranded RNA or bulge structures relative to the pre-miRNA, i.e. the distance in nucleotides should be carefully maintained. Secondary RNA structures for a particular RNA nucleotide sequence can easily be predicted using software tools and algorithms well known in the art such as MFOLD (Zucker et al. 2003 Nucleic Acids Research 31, 3406-3415). Furthermore, it is well within the skill of the art to design or modify a nucleotide by substituting nucleotides in a nucleotide sequence such that the newly introduced nucleotides exhibit more or less complementarity to another part of the nucleotide sequence and in this way influence the generation of double-stranded RNA stems or of single stranded RNA bulges.

It is also an object of the invention to provide eukaryotic host cells, plant cells, non-human eukaryotic organisms and plants containing the combination of inhibitory RNA molecules according to the invention. Gametes, seeds, embryos, either zygotic or somatic, progeny or hybrids of plants comprising the combination of inhibitory RNA molecules of the present invention, which are produced by traditional breeding methods are also included within the scope of the present invention.

As used herein, "artificially introduced dsRNA molecule" refers to the direct introduction of dsRNA molecule, which may e.g. occur exogenously or endogenously by transcription from a chimeric gene encoding such dsRNA molecule, however does not refer to the conversion of a single stranded RNA molecule into a dsRNA inside the eukaryotic cell or plant cell.

The methods and means described herein are believed to be suitable for all plant cells and plants, gymnosperms and angiosperms, both dicotyledonous and monocotyledonous plant cells and plants including but not limited to *Arabidopsis*, alfalfa, barley, bean, corn or maize, cotton, flax, oat, pea, rape, rice, rye, safflower, sorghum, soybean, sunflower, tobacco and other *Nicotiana* species, including *Nicotiana benthamiana*, wheat, asparagus, beet, broccoli, cabbage, carrot, cauliflower, celery, cucmber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, *papaya*, passion fruit, peach, peanut, pear, pineapple, pistachio, plum, raspberry, strawberry, tangerine, walnut and watermelon *Brassica* vegetables, sugarcane, vegetables (including chicory, lettuce, tomato), Lemnaceae (including species from the genera *Lemna*, Wolffiella, Spirodela, Landoltia, Wolffia) and sugarbeet.

The methods according to the invention are also believed to be applicable to other eukaryotic cells. The eukaryotic organism may thus also be a fungus, yeast or mold or an animal such as a human, mammal, fish, cattle, goat, pig, sheep, rodent, hamster, mouse, rat, guinea pig, rabbit, primate, nematode, shellfish, prawn, crab, lobster, insect, fruit fly, Coleapteran insect, Dipteran insect, Lepidopteran insect and Homeopteran insect. The cell may be in the organism or derived from the organism. The cell may be in cell culture or in a tissue or organ in vitro. In a preferred embodiment, if the cell is a human cell or if the cell is an animal cell (including human cells) the cell is in culture. The cell may be a somatic cell, stem cell, haematopoietic cell, nerve cell, fibroblast, endothelial cell, cancer cell, a cell of an immortalized cell line, or a cell which is or capable of being infected by a virus. The cell may be a liver cell, heart cell, kidney cell, brain cell, eye cell, nerve cell, skin cell, muscle cell, bone cell or other cell derived from the human or other animal body.

Introduction of chimeric genes (or RNA molecules) into the host cell can be accomplished by a variety of methods including calcium phosphate transfection, DEAE-dextran mediated transfection, electroporation, microprojectile bombardment, microinjection into nuclei and the like.

Methods for the introduction of chimeric genes into plants are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

Transgenic animals can be produced by the injection of the chimeric genes into the pronucleus of a fertilized oocyte, by transplantation of cells, preferably undifferentiated cells into a developing embryo to produce a chimeric embryo, transplantation of a nucleus from a recombinant cell into an enucleated embryo or activated oocyte and the like. Methods for the production of trangenic animals are well established in the art and include US patent 4, 873, 191; Rudolph et al. 1999 (Trends Biotechnology 17:367-374); Dalrymple et al. (1998) Biotechnol. Genet. Eng. Rev. 15: 33-49; Colman (1998) Bioch. Soc. Symp. 63: 141-147; Wilmut et al. (1997) Nature 385: 810-813, Wilmut et al. (1998) Reprod. Fertil. Dev. 10: 639-643; Perry et al. (1993) Transgenic Res. 2: 125-133; Hogan et al. Manipulating the Mouse Embryo, $2^{nd}$ ed. Cold Spring Harbor Laboratory press, 1994 and references cited therein.

Gametes, seeds, embryos, progeny, hybrids of plants or animals comprising the chimeric genes of the present invention, which are produced by traditional breeding methods are also included within the scope of the present invention.

As used herein, "the nucleotide sequence of gene of interest" usually refers to the nucleotide sequence of the DNA strand corresponding in sequence to the nucleotide sequence of the RNA transcribed from such a gene of interest unless specified otherwise.

It will be clear that the above methods can be applied to eukaryotic cells in vivo or in vitro. Furthermore, the methods as herein described when applied to animal or humans may encompass therapeutic, diagnostic and non-therapeutic and non-diagnostic methods. The combinations of artificial nucleic acids such as the inhibitory RNA molecules as herein described may also be used as medicaments for the purpose of the above mentioned therapeutic methods. Accordingly, the invention provides also a composition comprising at least two inhibitory RNA molecules as herein defined, as well as a kit comprising such a combination of nucleic acids as a combined preparation for simultaneous, separate or sequential use in therapeutic methods.

The following non-limiting Examples describe methods and means according to the invention. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R.D.D. Croy, jointly published by BIOS Scientific Publications Ltd (UK) and Blackwell Scientific Publications, UK. Other references for standard molecular biology techniques include Sambrook and Russell (2001) *Molecular Cloning: A Laboratory Manual*, Third Edition, Cold Spring Harbor Laboratory Press, NY, Volumes I and II of Brown (1998) *Molecular Biology LabFax*, Second Edition, Academic Press (UK). Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

EXAMPLES

Example 1

Combination of PolII-Transcribed and PolIII-Transcribed Chimeric Genes Directed Against a Reporter Gene To test if a combination of hpRNA-encoding transgenes comprising one expressed from a promoter recognized by RNA polymerase II (eg. a CaMV35S promoter) and another expressed from a promoter recognized by RNA polymerase III (eg. an AtU6 promoter) would enhance the effectiveness of silencing of a target gene, crosses were made between *Arabidopsis* plants comprising either a 35S- or an AtU6-PDShp42 inhibitory RNA-encoding transgenes and progeny plants comprising both transgenes were identified and the extent of silencing of the PDS target gene compared to plants containing only one of the transgenes. In a similar way, crosses were made between *Arabidopsis* plants expressing either 35S- or AtU3-driven GUS hpRNA transgenes to compare the effectiveness of the combination compared to the single transgenes.

a) Chimeric Genes

Transgenic *Arabidopsis* lines comprising 35S- or AtU6-directed PDShp42 and 35S- or AtU3-directed hpGUS transgenes have been described in detail in WO2004/073390 (herein incorporated by reference; see particularly Example 2 and Example 5).

Briefly, to produce the PDShp42 chimeric genes, oligonucleotides were annealed to generate a double-stranded DNA fragment which when transcribed would yield an RNA transcript having self-complementarity (complementary sense and antisense regions each of 42 nucleotides) such that the transcript on folding had a double-stranded (duplex) region of 42 contiguous basepairs joined by a 9nt single-stranded loop. The nucleotide sequence of the sense region corresponded to part of the sequence (nucleotides 1570 to 1611 of AT4G14210.2 available at www.arabidopsis.org/servlets/TairObject?type=locus&name=AT4G14210) of the phytoene-desaturase gene of *Arabidopsis* and the antisense region corresponded to the complement of the 42 nucleotides. The DNA fragment was operably linked to either a CaMV35S promoter sequence and an octopine synthase 3' end region (transcription termination/polyadenylation signal) or to a promoter of the U6 small RNA gene of *A. thaliana* and an oligo dT sequence (8 T's) which was able to function as a transcription terminator for a Pol III type promoter. When silencing constructs were transferred to *A. thaliana*, effective down-regulation of the expression of the endogenous PDS gene resulted in leaves that exhibited photobleaching (see e.g. FIG. 1B). The extent of photobleaching was an indicator of the extent of the gene silencing and therefore the effectiveness of the silencing construct(s).

To produce the GUShp92-encoding chimeric genes, a GUS inverted repeat DNA sequence was synthesized which comprised 186 nucleotides corresponding to sense sequence of the GUS gene (nt 512-697 of GUS ORF) fused at the 3' end with an antisense sequence corresponding to the first 93 nucleotides of the 186 nt fragment (nucleotides 512-604 of the GUS ORF). Transcription of the GUS inverted repeat sequence therefore produced an RNA with complementary sense and antisense regions, able to hybridize to form a duplex region of 93 basepairs, joined by a single-stranded loop. This inverted repeat sequence was either linked operably to a CaMV35S promoter sequence and an octopine synthase 3' end region, or to a promoter of the U3 small RNA gene of *A. thaliana* and an oligo dT sequence (9 T's) for transcription termination, or to a promoter of the U6 small RNA gene of *A. thaliana* and an oligo dT sequence. When transferred to *A. thaliana* comprising a CaMV35S-GUS transgene as a target gene, the efficiency of down-regulation of the GUS gene by the inhibitory RNA encoding chimeric genes or combination thereof was measured using conventional GUS assays using MUG as substrate.

b) Northern Analysis

A Northern blot analysis showed that the hpRNAs produced from the two types of GUShp93 transgenes were differentially processed into shorter forms in the transgenic plants (FIG. 2). The 35S lines showed predominantly the 21 nt species (FIG. 2, panel A lanes 1-6, panel B lanes 1,2,4,6), while the U6 lines showed the 24 nt and/or 22 nt species (FIG. 2, panel A 7-22, panel B 8, 9, 10, 11, 12, 15-18 and 22). Furthermore, differences were seen in the patterns of the intermediate RNA processing species. The 35S-GUShp93 lines showed a predominant RNA species of ~90 nt corresponding to the loop of the GUShp93 RNA, whereas in the U6-GUShp93 lines the predominant fragment was the full-length GUShp93 RNA.

Figure 1:
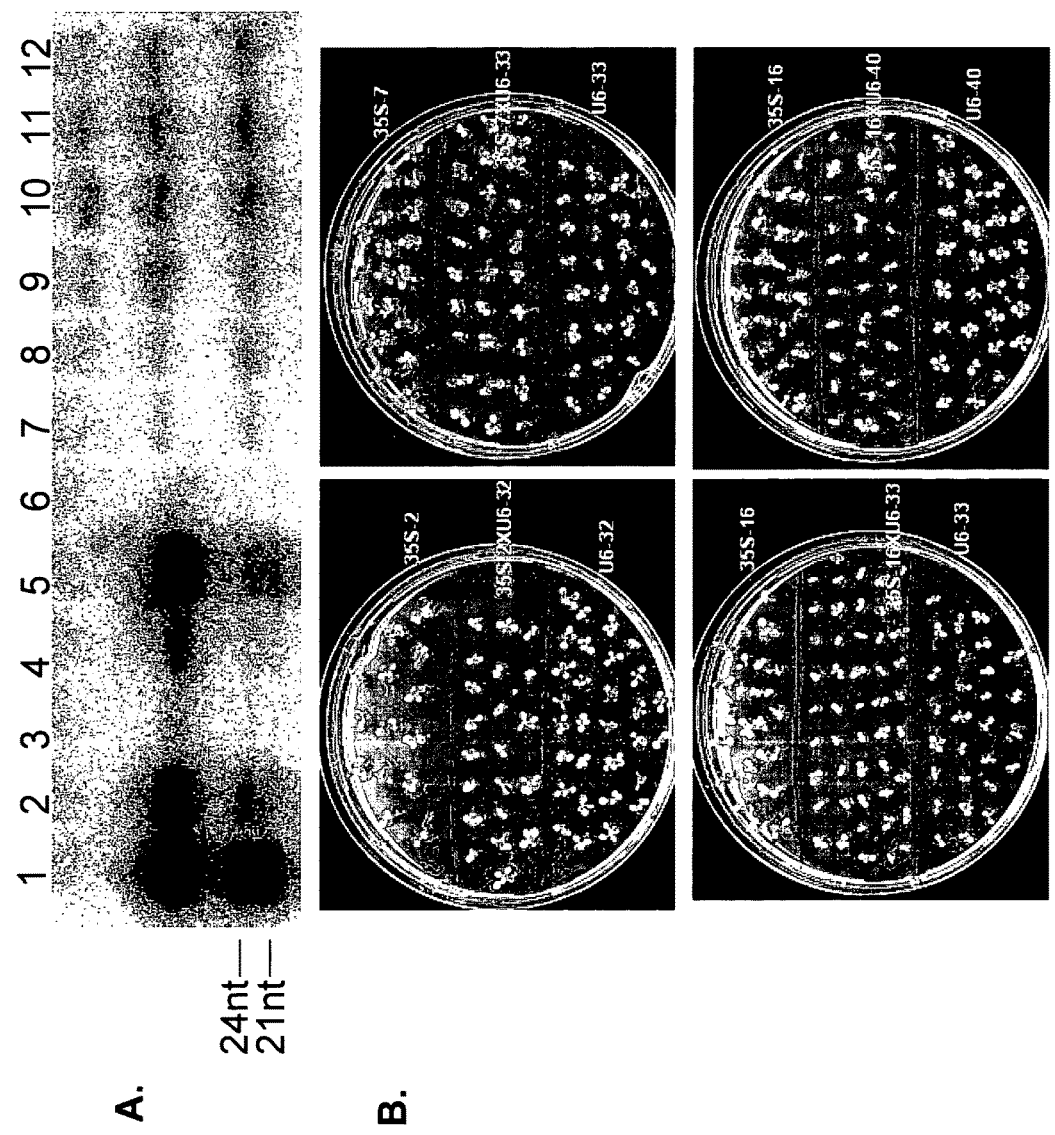
FIG. 1. Panel A: Short hpRNAs derived from CaMV35S (Poll II recognized) and AtU6-directed (Pol III recognized) PDShp42 transgenes are differentially processed: the patterns of both the intermediate RNA species and the siRNAs are different between the 35S and the U6 lines. Lane 1-6: Northern analysis of small RNA species in different plant lines comprising the CaMV35S driven PDS hp42 transgenes; lanes 7-12 Northern analysis of small RNA species in different plant lines comprising the AtU6 driven PDS hp42 transgenes.

Similarly, a Northern blot analysis showed that the hpRNAs produced from the two types of PDShp42 transgenes were also differentially processed into shorter forms (FIG. 1A). Indeed, lanes 1-6 (corresponding to plants comprising the 35S promoter-driven transgene) showed both 24 nt and 21 nt long siRNA species, whereas lanes 7-12 (corresponding to plants comprising the U6 promoter-driven PDShp42 transgene) showed only the 24 nt species. Furthermore, differences were seen in the patterns of the intermediate RNA processing species.

Taken together, these results indicated that the U6 and 35S-transcribed hpRNAs were processed differently, with the U6 driven transcript processed predominantly, if not entirely, by the DCL3 and/or DCL2-dependent processing pathway while the 35S driven transcript was processed predominantly by the DCL4 and/or DCL3 pathways. This also indicated that the observed 35S- and AtU6-hpRNA directed silencing worked through different pathways. Plants were therefore analyzed to establish whether the combination of the two types of constructs would provide improved silencing in extent and/or duration and/or stability.

c) Phenotypic Analysis of Plants Comprising Both Types of Hp-Transgenes.

Heterozygous parental plants containing the 35S-PD-Shp42 transgene (male) were crossed with parental plants heterozygous for the AtU6-PDShp42 transgene (female) and F1 progeny plants comprising both transgenes were obtained and compared to parental plants containing one or the other of the transgenes.

| PolII line | PolIII line | F1 seed obtained |
|---|---|---|
| 35S-PDShp42 | AtU6-PDShp42 | 35S-2 × U6-32 |
| | | 35S-2 × U6-36 |
| | | 35S-7 × U6-33 |
| | | 35S-7 × U6-40 |
| | | 35S-16 × U6-33 |
| | | 35S-16 × U6-40 |
| | | 35S-19 × U6-32 |
| | | 35S-19 × U6-36 |

Based on the intensity of leaf bleaching, the F1 plants from at least four of the crosses showed a greater extent of PDS gene silencing compared to the parental U6 lines (FIG. 1B).

In a similar way, plants containing the 35S-GUShp93 transgenes were crossed with plants containing the AtU6-GUShp93 or AtU3-GUShp93 transgene and progeny comprising both transgenes was obtained. F2 lines resulting from selfing of the F1 population were identified by PCR from the crosses between 35S- and AtU3/AtU6-directed GUShp93 lines, which contained either the individual 35S- or Pol III-directed transgene or both of the two types of transgenes. The F2 lines would have been either homozygous or heterozygous (segregating) for the genes encoding the inhibitory RNAs. Although copy number effects could not be excluded in this experiment an average extent of silencing could be determined by analyzing sufficient lines.

| PolII line | PolIII line | F1 obtained | F2 obtained |
|---|---|---|---|
| 35S-GUShp93 (pMBW479) | AtU6 + 20-GUShp93 (pMBW488) | 479-A × 488-6 | 479-A × 488-6 |
| | | 488-13 × 479-1 | 488-13 × 479-1 |
| | | 479-1 × 488-6 | 479-4 × 488-1 |
| | | 479-4 × 488-1 | 488-1 × 479-2 |
| | | 488-1 × 479-2 | |
| 35S-GUShp93 (pMBW479) | AtU6-GUShp93 (pMBW486) | 479-5 × 486-2 | 486-2 × 479-4 |
| | | 486-2 × 479-4 | |
| 35S-GUShp93 (pMBW479) | AtU3 + 136-GUShp93 (pMBW480) | 479-1 × 480-2 | 479-1 × 480-2 |
| | | 479-4 × 480-6 | |
| 35S-GUShp93 (pMBW479) | AtU3-GUShp93 (pMBW481) | 479-2 × 481-1 | 479-5 × 481-8 |
| | | 479-5 × 481-8 | |

The different transgenic plants comprising either individual transgenes or the combination thereof are analyzed for GUS expression. Analysis of F3 plants from one cross (479-A×488-6) revealed that these plants appeared to have more uniform silencing than those containing only one transgene. The results of the MUG assay for different F3 plants from a 35S-GUShp93×U6-GUShp93 cross are graphically represented in FIG. 3.

The differences in the processing pathways used by the PolII and PolIII transcripts was apparently related not only to the different promoters used—PolIII promoters are active preferentially in the nucleolar region of the nucleus, while PolII promoters are active in other regions of the nucleus—but also to the structure of the transcripts. The PolII transcripts also contain a 5'leader portion derived from transcription of the 35S promoter that was used to make the construct, as well as a 3' UTR region derived by transcription of the ocs 3' terminator that was used, and a polyA tail. These additional 5' and 3' sequences amounted to 200-300 nt for the polII transcript produced by the 35S construct. In contrast, the U6 constructs that were made expressed a transcript comprising the hairpin portion (duplex region plus the single-stranded loop) with an additional 5' region of approximately 20 nt, but without any polyA tail. Therefore, the PolII and PolIII transcripts would fold into quite different structures. RNA transcripts are thought to be bound by double-stranded RNA binding proteins (DRBP) soon after transcription, and the different transcripts might be bound by different DRBPs, leading to differential access to DCL proteins and incorporation into different types of RISC complexes. This in turn was expected to lead to different contributions to transcriptional gene silencing (TGS), involving in particular methylation of promoter regions, and PTGS. It is thought that PolIII driven transcripts which produce 24mers corresponding to promoter regions are particularly effective in mediating TGS.

Example 2

Combination of microRNA and hpRNA Directed Against PHYB Endogenous Gene

A first chimeric gene encoding an inhibitory hpRNA directed against a Phytochrome B coding region of *Arabidopsis* was constructed using conventional recombinant DNA techniques by operably linking the following DNA regions in order: a promoter region, a DNA region which when transcribed yields a sense RNA molecule, corresponding to the sequence of the PHYB coding region from nucleotide 789 to nucleotide 809 of Accession No. EF193580, an antisense RNA molecule complementary to the sense RNA molecule, and a 3'end region.

Using conventional recombinant DNA techniques a second chimeric gene was constructed comprising a transcribed region encoding a pri-microRNA miR159 scaffold, wherein the microRNA region was adapted to comprise a nucleotide sequence (SEQ ID NO:1 TTATAAGTTTCATGAAGATGA) from the PHYB coding region and corresponding changes were made in the micro RNA* region. The coding region of the pre-microRNA was operably linked to a plant-expressible promoter and transcription termination region.

The chimeric genes were introduced separately into T-DNA vectors accompanied by a selectable marker gene and transgenic *Arabidopsis* plants were produced that comprised either of the chimeric genes (Figure ZZ). Transgenic F1 plants comprising both chimeric genes were also generated by crossing the initial transformants. These plants are then selfed to produce F2 seed which will be analyzed for the extent of silencing. The degree of silencing can be determined by measuring the length of the hypocotyls of seedlings grown from the seed under white-light. The longer the hypocotyls, the stronger the degree of silencing of the PHYB gene, since PHYB is a repressor of hypocotyl extension under white light.

Plants containing both transgenes exhibit a higher degree of silencing of the PHYB gene than plants containing each of the transgenes separately.

Example 3

Combination of Sense RNA Directed Towards EIN2 Promoter Region and hpRNA Directed Towards EIN2 Coding Region and Promoter To examine if co-expression of sense RNA-encoding and hpRNA-encoding transgenes would induce stronger promoter silencing (TS) than either construct alone, two constructs were produced. Both targeted the promoter region of the *Arabidopsis* EIN2 gene, however the hpRNA construct further comprised part of the transcribed region of the EIN2 gene in the duplex portion. Transgenic plants comprising the hpRNA promoter construct were crossed with plants comprising the sense promoter construct. The extent of EIN2 silencing was assayed on the F2 population by comparison with the parental lines. The results indicated that the combination of the sense- and hpRNA-EIN2 transgenes targeting the EIN2 promoter region yielded greater silencing than the hpRNA- or sense RNA-encoding transgene alone (FIG. 2).

a) Chimeric Genes

A first chimeric gene encoding a sense RNA targeted towards the EIN2 gene promoter was constructed using conventional recombinant DNA techniques, and comprised the following operably linked DNA regions: a promoter region, a DNA region which when transcribed yielded an RNA molecule corresponding to nt. 1-1217 of the full-length sequence of the EIN2 gene (Accession number AF141202)—including part of the promoter region (~810 bp)—, and a 3'end region from octopinesynthase gene.

A second chimeric gene encoding a hairpin RNA targeted towards the EIN2 gene promoter was constructed comprising the following operably linked DNA regions: a promoter region, a DNA region which when transcribed yields a sense RNA molecule corresponding to the sequence of the EIN2 gene (from nucleotide 1 to nucleotide 1217) including part of the promoter region and part of the transcribed DNA region and a antisense RNA molecule complementary to the sense RNA molecule, and a ocs 3'end region.

The chimeric genes were inserted into a T-DNA vector accompanied by a selectable marker gene (either neomycin phosphotransferase or hygromycin transferase) and transgenic *A. thaliana* plants comprising the chimeric genes were generated.

b) Phenotypic Analysis

Silencing of the expression of EIN2 will be assayed by germinating transgenic seeds comprising either one of the transgenes or a combination of both on medium containing ACC (amino-cyclopropane-1-carboxylic acid) in the dark. The results of such assays are indicated in FIG. 4B, indicating that the extent of EIN2 silencing was enhanced in some of the sense×hpRNA crosses when compared to the silencing achieved in the parental lines.

c) Northern Analysis

Northern Blot analysis of small RNAs isolated from the transgenic plants showed that siRNAs accumulated in the presence of the EIN2 promoter-targeted constructs (FIG. 4A), indicating that the EIN2 promoter constructs were correctly made and properly expressed. Interestingly, in two out of the four groups of sense, hpRNA and sense×hpRNA lines analysed, the sense×hpRNA crosses (hp-2×s-2 and hp-3×s-3, indicated by arrows) appeared to accumulate more siRNAs than their corresponding sense (s) and hpRNA (hp) parental lines (FIG. 4A). This was consistent with the phenotypic results for EIN2 silencing shown in FIG. 4B, where EIN2 silencing was enhanced in some of the progeny plants produced from the sense×hpRNA crosses.

A possible improvement on the hpRNA and sense combination strategy is to use different promoters to drive the expression of hpRNA and sense transgenes respectively. This can minimize transcriptional silencing of the transgenes which is more likely to occur if the same promoter is used for both transgenes.

The present application claims priority from European Application No. 07015956.1 and U.S. Provisional Application No. 61/013,604, the entire contents of which are incorporated herein by reference.

All publications discussed and/or referenced herein are incorporated herein in their entirety.

The invention claimed is:

1. A method to reduce the expression of a target nucleic acid in a plant cell or plant comprising the step of introducing a combination of two inhibitory RNA molecules each capable of reducing the expression of a first target nucleic acid in said plant cell or plant, wherein one of said inhibitory RNA molecules is an artificial miRNA molecule, an artificial pre-microRNA molecule comprising said artificial miRNA or an artificial pri-miRNA molecule comprising said artificial miRNA, said artificial miRNA being capable of reducing the expression of the first target nucleic acid, wherein said artificial miRNA comprises 20 nucleotides with a nucleotide sequence essentially complementary to the target nucleic acid whereby one or more of the following mismatches may occur:

a. a mismatch between a nucleotide at the 5' end of said miRNA and the corresponding nucleotide sequence in the target nucleic acid;

b. a mismatch between any one of the nucleotides in position 1 to position 9 of said miRNA and the corresponding nucleotide sequence in the target nucleic acid; or c. three mismatches between any one of the nucleotides in position 12 to position 21 of said miRNA and the corresponding nucleotide sequence in the target nucleic acid provided that there are no more than two consecutive mismatches;

provided no mismatch occurs at positions 10 and 11 of the miRNA, and wherein said other inhibitory RNA molecule is a hairpin double stranded RNA molecule comprising a first and second RNA region which are complementary or essentially complementary to each other, said first RNA region comprising 19 consecutive nucleotides corresponding to a nucleotide sequence of the first target nucleic acid and said second RNA region comprising at least 19 consecutive nucleotides corresponding to a nucleotide sequence complementary to the nucleotide sequence of the first target nucleic acid, wherein said first and second RNA regions hybridize to each other with at least 18 or 19 basepairs.

2. The method according to claim 1, wherein the two inhibitory RNA molecules target the same region, overlapping regions, or non-overlapping regions of the first target nucleic acid.

3. The method according to claim 1, wherein the two inhibitory RNA molecules are not covalently joined.

4. The method according to claim 1, wherein the two inhibitory RNA molecules are expressed from different promoters.

5. The method according to claim 1, wherein one of said inhibitory RNA molecules comprises at least 19 consecutive nucleotides from a promoter region of the target nucleic acid molecule, and said other inhibitory RNA molecule comprises at least 19 consecutive nucleotides from the region of the target nucleic acid molecule which is transcribed into a RNA molecule.

6. The method according to claim 1, wherein said inhibitory RNA molecules are transcribed from chimeric genes introduced in said plant cell.

7. The method according to claim 1, wherein one of said inhibitory RNA molecules is transcribed from a chimeric-gene under control of a promoter recognized by RNA polymerase II and said other inhibitory RNA is transcribed from a chimeric gene under control of a promoter recognized by RNA polymerase III.

8. The method according to claim 1, wherein said target nucleic acid is a viral nucleic acid or a gene or transcribed region thereof.

9. The method according to claim 1, wherein said target nucleic acid is a transgene or a region thereof.

10. The method according to claim 1, wherein said target nucleic acid is an endogenous gene in the cell, a promoter thereof, a transcript thereof or a region thereof.

11. The method according to claim 1, wherein the combination of two inhibitory RNA molecules reduces the expression of the first target nucleic acid to a greater extent than either inhibitory RNA molecule alone in said eukaryotic cell or organism.

12. A plant cell comprising two inhibitory RNA molecules capable of reducing the expression of a first target nucleic acid in said cell, wherein one of said inhibitory RNA molecules an artificial miRNA molecule, an artificial pre-microRNA molecule comprising said artificial miRNA or an artificial pri-miRNA molecule comprising said artificial miRNA, said artificial miRNA being capable of reducing the expression of the first target nucleic acid, wherein said artificial miRNA comprises 20 nucleotides with a nucleotide sequence essentially complementary to the target nucleic acid whereby one or more of the following mismatches may occur:

a. a mismatch between a nucleotide at the 5' end of said miRNA and the corresponding nucleotide sequence in the target nucleic acid;

b. a mismatch between any one of the nucleotides in position 1 to position 9 of said miRNA and the corresponding nucleotide sequence in the target nucleic acid; or c. three mismatches between any one of the nucleotides in position 12 to position 21 of said miRNA and the corresponding nucleotide sequence in the target nucleic acid provided that there are no more than two consecutive mismatches;

provided no mismatch occurs at positions 10 and 11 of the miRNA, and wherein said other inhibitory RNA molecule is a hairpin double stranded RNA molecule comprising a first and second RNA region which are complementary or essentially complementary to each other, said first RNA region comprising at least 19 consecutive nucleotides corresponding to a nucleotide sequence of the first target nucleic acid and said second RNA region comprising at least 19 consecutive nucleotides corresponding to a nucleotide sequence complementary to the nucleotide sequence of the first target nucleic acid, wherein said first and second RNA regions hybridize to each other with at least 18 or 19 basepairs.

13. The plant cell according to claim 12, wherein the two inhibitory RNA molecules target the same region, overlapping regions, or non-overlapping regions of the first target nucleic acid.

14. The plant cell according to claim 12, wherein the two inhibitory RNA molecules are not covalently joined.

15. The plant cell according to claim 12, wherein the two inhibitory RNA molecules are expressed from different promoters.

16. The plant cell according to claim 12, wherein one of said inhibitory RNA molecules comprises at least 19 consecutive nucleotides from a promoter region of said target nucleic acid molecule, and said other inhibitory RNA molecule comprises at least 19 consecutive nucleotides from the region of said target nucleic acid molecule which is transcribed into a RNA molecule.

17. The plant cell according to claim 12, wherein said inhibitory RNA molecules are transcribed from chimeric genes introduced in said plant cell.

18. The plant cell according to claim 12, wherein one of said inhibitory RNA molecules is transcribed from a chimeric gene under control of a promoter recognized by RNA polymerase II and said other inhibitory RNA is transcribed from a chimeric gene encoding gene under control of a promoter recognized by RNA polymerase III.

19. The plant cell according to claim 12, wherein said target nucleic acid is a viral nucleic acid or a gene or transcribed region thereof.

20. The plant cell according to claim 12, wherein said target nucleic acid is a transgene or a region thereof.

21. The plant cell according to claim 12 wherein said target nucleic acid is an endogenous gene in the cell, a promoter thereof, a transcript thereof or a region thereof.

22. A plant consisting essentially of plant cells according to claim 12.

23. The plant of claim 22, wherein the combination of two inhibitory RNA molecules reduces the expression of the first target nucleic acid to a greater extent than either inhibitory RNA molecule alone in said eukaryotic cell or organism in said eukaryotic organism.

* * * * *